(12) United States Patent
Woodcock et al.

(10) Patent No.: US 11,939,345 B2
(45) Date of Patent: Mar. 26, 2024

(54) PHYSIOLOGICALLY STABLE FLUOROPHORE AND PERFORMING FLUORESCENCE PROBING

(71) Applicant: Government of the United States of America, as represented by the Secretary of Commerce, Gaithersburg, MD (US)

(72) Inventors: Jeremiah Wallace Woodcock, Gaithersburg, MD (US); Jeffrey William Gilman, Mt. Airy, MD (US); Douglas Matthew Fox, Reston, VA (US)

(73) Assignee: GOVERNMENT OF THE UNITED STATES OF AMERICA, AS REPRESENTED BY THE SECRETARY OF COMMERCE, Gaithersburg, MD (US)

( * ) Notice: Subject to any disclaimer, the term of this patent is extended or adjusted under 35 U.S.C. 154(b) by 500 days.

(21) Appl. No.: 17/117,424

(22) Filed: Dec. 10, 2020

(65) Prior Publication Data
US 2021/0179639 A1      Jun. 17, 2021

Related U.S. Application Data

(60) Provisional application No. 62/948,902, filed on Dec. 17, 2019.

(51) Int. Cl.
| | | |
|---|---|---|
| A61B 5/00 | (2006.01) | |
| A61B 8/00 | (2006.01) | |
| A61B 10/00 | (2006.01) | |
| A61K 49/00 | (2006.01) | |
| C07F 5/02 | (2006.01) | |
| C08B 11/16 | (2006.01) | |
| C08L 1/30 | (2006.01) | |

(52) U.S. Cl.
CPC .......... *C07F 5/022* (2013.01); *A61K 49/0021* (2013.01); *C08B 11/16* (2013.01); *C08L 1/30* (2013.01)

(58) Field of Classification Search
CPC ..... C07F 5/022; A61K 49/0021; C08B 11/16; C08L 1/30
See application file for complete search history.

(56) References Cited

PUBLICATIONS

Feng et al. (Liquid Crystals 2018, 1470-1476).*
Kowada et al. (Chem. Soc. Rev. 2015, 44, 4953-4972).*
Monteiro et al. (Acta Biomater. 2015, 18, 196-205).*
Yuan, K., et al., "Impact of Ferrocene Substitution on the Electronic Properties of Bodipy Derivatives and Analogues", Inorganic Chemistry, 2018, p. 14698-14704, vol. 57.

* cited by examiner

*Primary Examiner* — Michael G. Hartley
*Assistant Examiner* — Melissa J Perreira
(74) *Attorney, Agent, or Firm* — Office of Chief Counsel for National Institute of Standards and Technology

(57) ABSTRACT

A physiologically stable fluorophore includes a terminal moiety including a terminal reactive site that reacts with a reactive group of a substrate; a stability linker covalently bonded to the terminal moiety; and a bridge moiety covalently bonded to the stability linker such that the stability linker is interposed through chemical bonds between the bridge moiety and the terminal moiety; and a fluorescent moiety covalently bonded to the bridge moiety of the redox moiety and including: an electron bandgap mediator that is covalently bonded to the bridge moiety; a coordinate center covalently bonded to the electron bandgap mediator and that forms a Zwitterionic member with an atom in the electron bandgap mediator; and a steric hinder bonded to the electron bandgap mediator to provide steric hindrance for protection of the coordinate center.

2 Claims, 22 Drawing Sheets

211

PHYSIOLOGICALLY STABLE FLUOROPHORE AND PERFORMING FLUORESCENCE PROBING

CROSS REFERENCE TO RELATED APPLICATIONS

The application claims priority to U.S. Provisional Patent Application Ser. No. 62/948,902 filed Dec. 17, 2019, the disclosure of which is incorporated herein by reference in its entirety.

STATEMENT REGARDING FEDERALLY SPONSORED RESEARCH

This invention was made with United States Government support from the National Institute of Standards and Technology (NIST), an agency of the United States Department of Commerce. The Government has certain rights in the invention. Licensing inquiries may be directed to the Technology Partnerships Office, NIST, Gaithersburg, MD, 20899; voice (301) 975-2573; email tpo@nist.gov; reference NIST Docket Number 19-047US1.

BRIEF DESCRIPTION

Disclosed is a physiologically stable fluorophore comprising: a terminal moiety comprising a terminal reactive site that reacts with a reactive group of a substrate to form a fluorophore-substrate complex, the fluorophore-substrate complex comprising the physiologically stable fluorophore covalently bonded to the substrate via the terminal moiety; a stability linker covalently bonded to the terminal moiety; and a bridge moiety covalently bonded to the stability linker such that the stability linker is interposed through chemical bonds between the bridge moiety and the terminal moiety; and a fluorescent moiety covalently bonded to the bridge moiety of the redox moiety and comprising: an electron bandgap mediator that is covalently bonded to the bridge moiety; a coordinate center covalently bonded to the electron bandgap mediator and that forms a Zwitterionic member with an atom in the electron bandgap mediator; and a steric hinder bonded to the electron bandgap mediator to provide steric hindrance for protection of the coordinate center.

Disclosed is a process for performing single-electron transfer fluorescence probing, the process comprising: contacting a substrate with the physiologically stable fluorophore, the substrate comprising the reactive group covalently bonded to a basal member; forming the fluorophore-substrate complex from the physiologically stable fluorophore and the substrate in response to contacting the substrate with the physiologically stable fluorophore; subjecting the probe-analyte complex to probe radiation; electronically exciting the physiologically stable fluorophore in the fluorophore-substrate complex in response to subjecting the fluorophore-substrate complex to the probe radiation; producing fluorescence from the physiologically stable fluorophore in the fluorophore-substrate complex in response to electronically exciting the physiologically stable fluorophore in the fluorophore-substrate complex; and determining, from the fluorescence from the physiologically stable fluorophore, the redox state of the substrate to perform single-electron transfer fluorescence probing.

BRIEF DESCRIPTION OF THE DRAWINGS

The following description should not be considered limiting in any way. With reference to the accompanying drawings, like elements are numbered alike.

DETAILED DESCRIPTION

Figure 1:
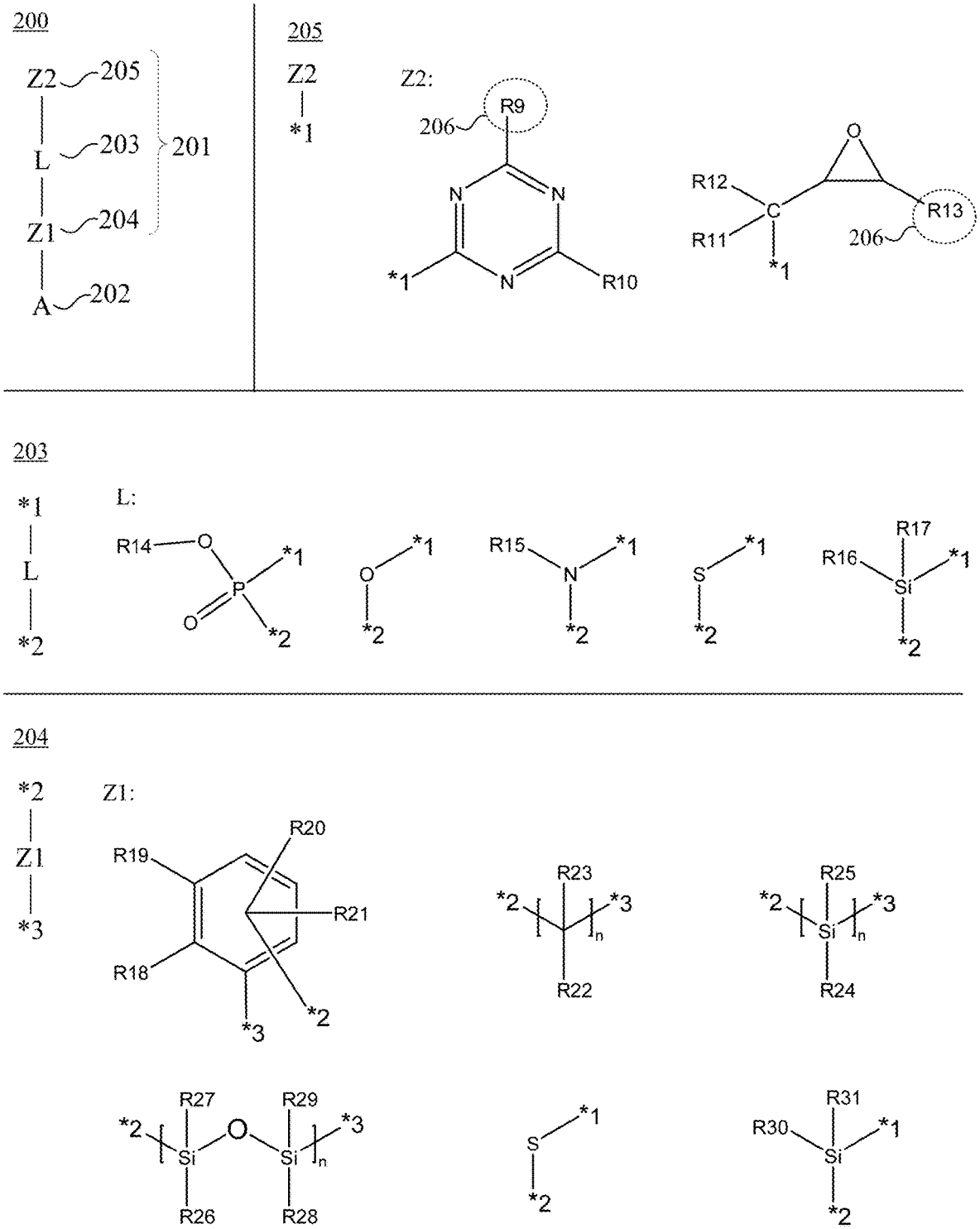
FIG. 1 shows structures of a physiologically stable fluorophore, terminal moiety, electron transfer metal, bridge moiety, and fluorescent moiety.
Figure 2:
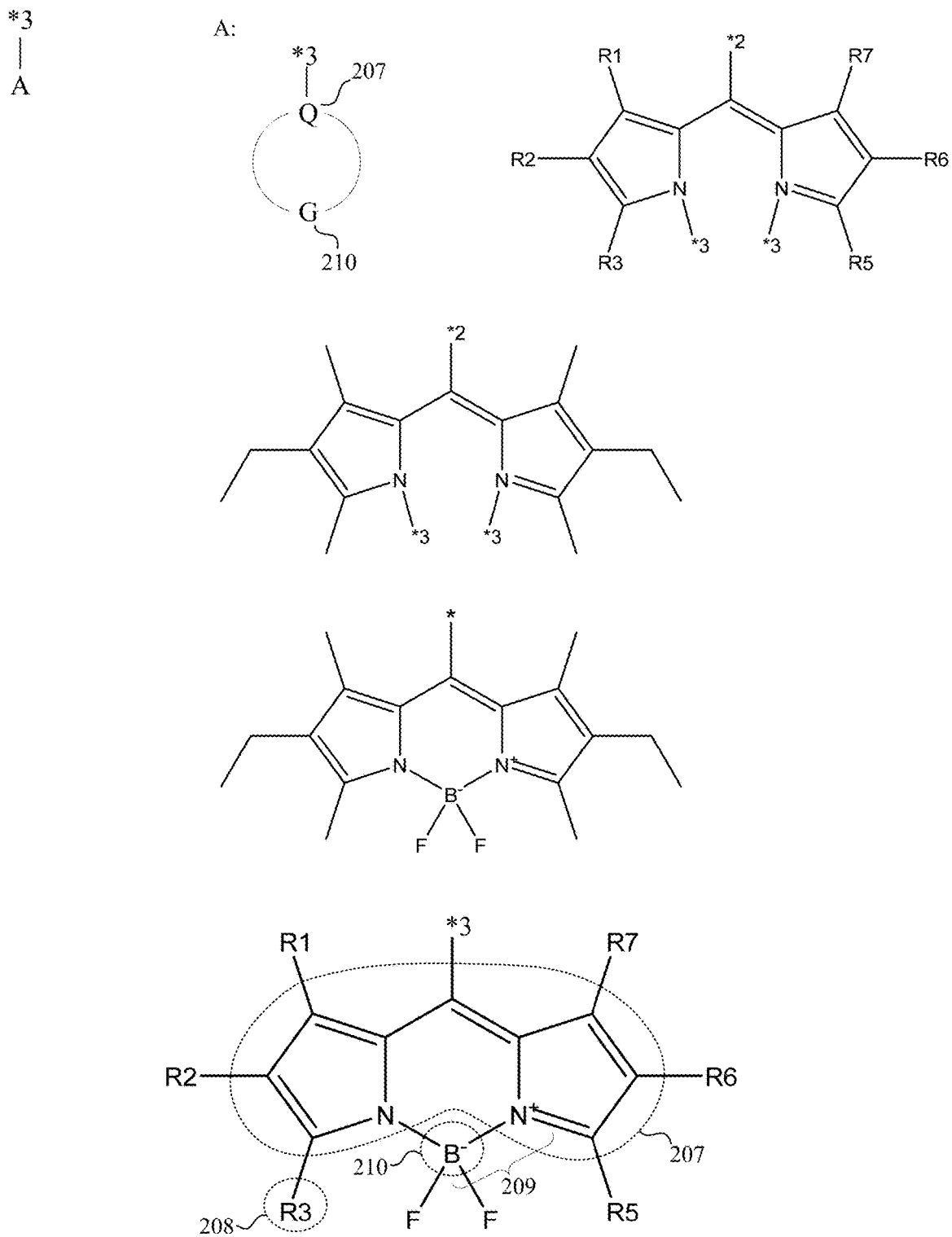
FIG. 2 shows a structure of a fluorescent moiety.
Figure 3:
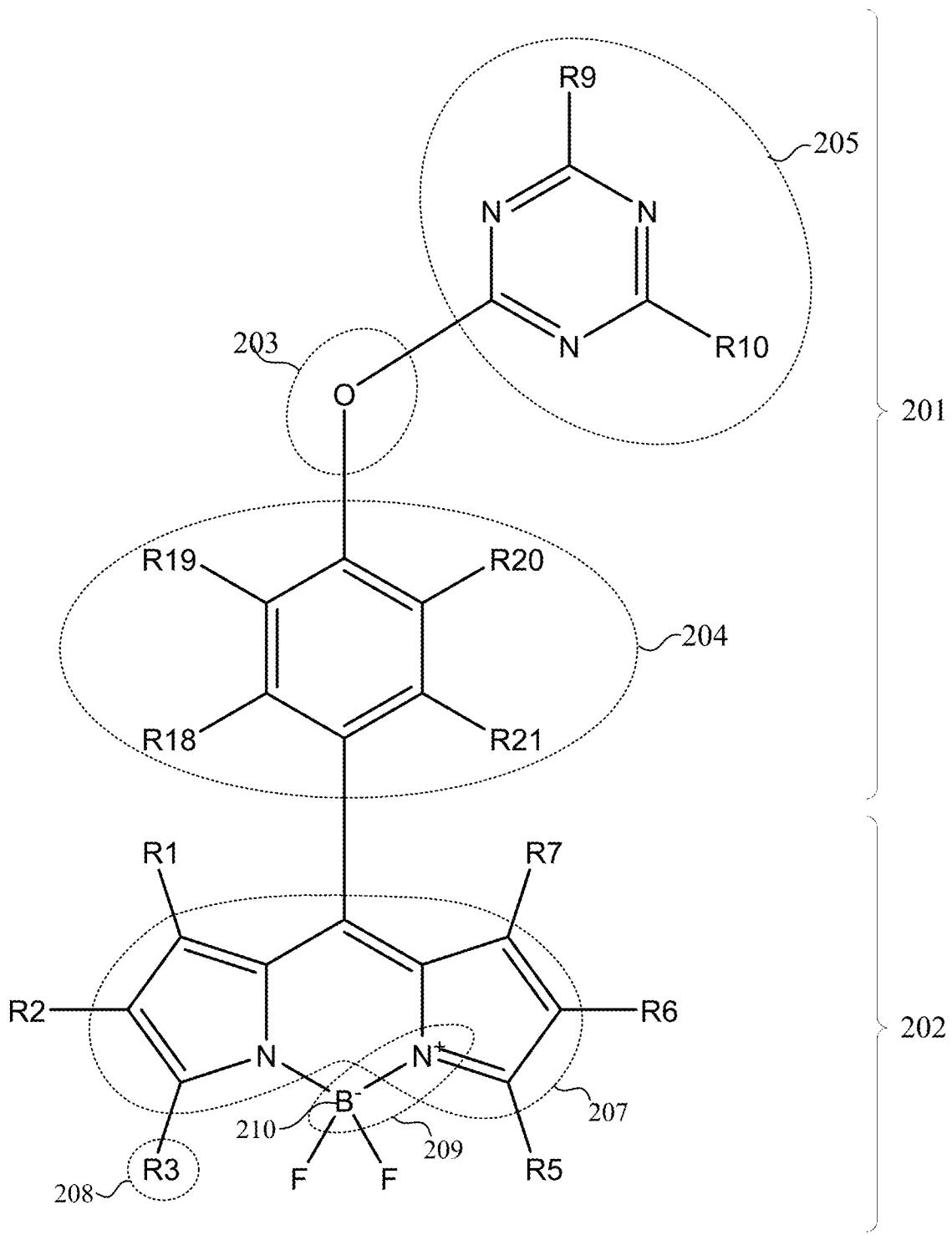
FIG. 3 shows a structure of a physiologically stable fluorophore.
Figure 4:
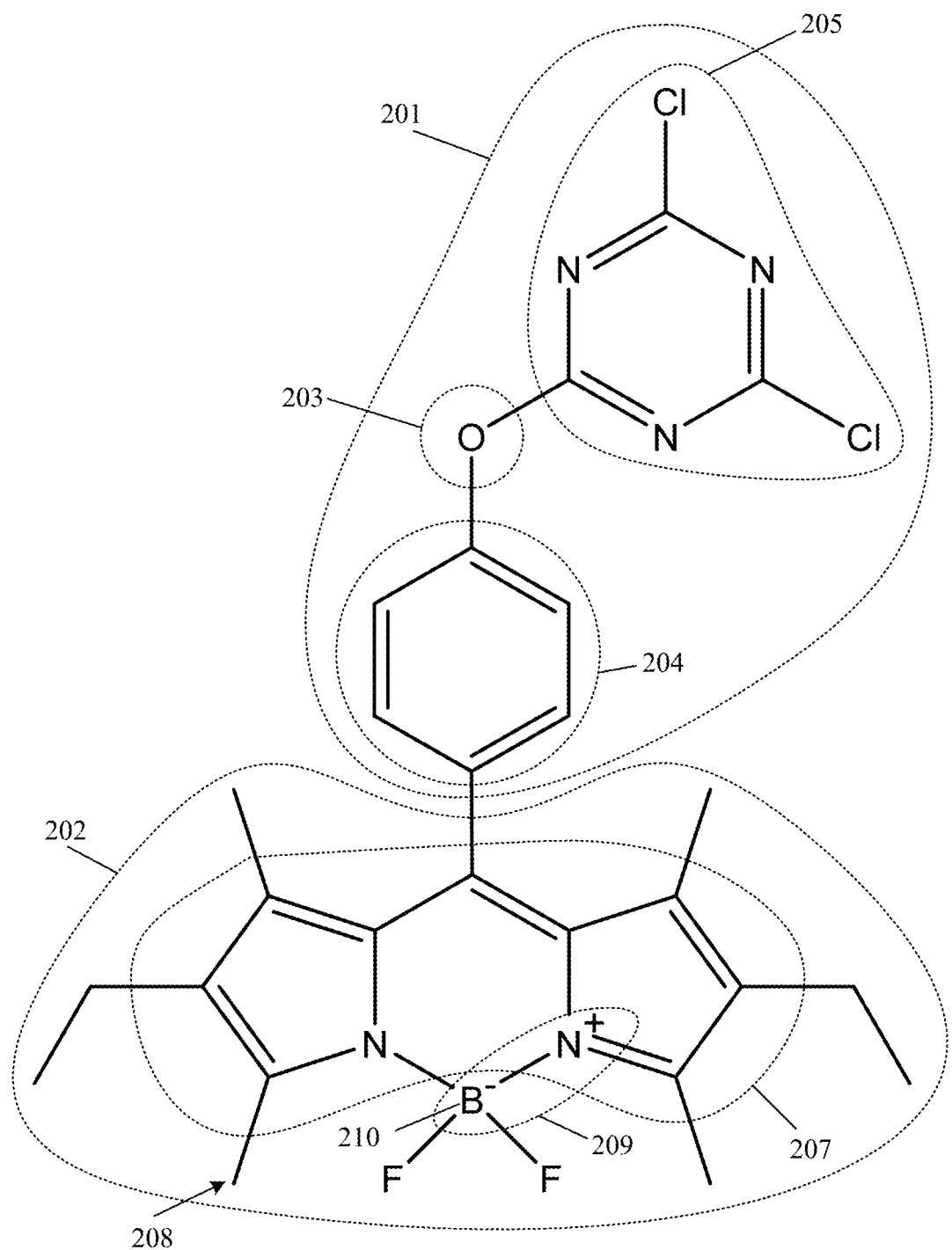
FIG. 4 shows a structure of a physiologically stable fluorophore.

A detailed description of one or more embodiments is presented herein by way of exemplification and not limitation.

Diversity of materials used industrially and demand for more renewable feed stocks has been increased over recent years. As a result, strategies to assay impact on the environment and human physiology are desired. Conventional methods for radioactive isotopic labeling and fluorescent labeling for tracking uptake and analyzing compounds after excretion have technical limitations. Isotopic labeling can be expensive, and conventional fluorescent dyes and attachment chemistry can be sensitive to pH fluctuations or enzymatic attack. A physiologically stable fluorophore described herein overcomes limitations of conventional fluorophores that are susceptible changes due to pH because the physiologically stable fluorophore is highly resistant to pH fluctuations found in the digestive system of mammals, e.g., humans, and is resistant to enzymatic attack that causes chemical degradation of conventional fluorophore compounds. The physiologically stable fluorophore retains its fluorescent properties during of digestion in the digestive system and provides with enables the pathway and absorbance rate of materials to readily be tracked.

Physiologically stable fluorophore 200 can be used for performing fluorescence probing. In an embodiment, with reference to FIG. 1, FIG. 2, FIG. 3, FIG. 4, FIG. 5, and FIG. 6, physiologically stable fluorophore 200 includes: redox moiety 201 including: terminal moiety 205 including terminal reactive site 206 that reacts with reactive group 213 of substrate 211 to form fluorophore-substrate complex 212, fluorophore-substrate complex 212 including physiologically stable fluorophore 200 covalently bonded to substrate 211 via terminal moiety 205; stability linker 203 covalently bonded to terminal moiety 205; and bridge moiety 204 covalently bonded to stability linker 203 such that stability linker 203 is interposed through chemical bonds between bridge moiety 204 and terminal moiety 205; and fluorescent moiety 202 covalently bonded to bridge moiety 204 of redox moiety 201 and including: electron bandgap mediator 207 that is covalently bonded to bridge moiety 204; coordinate center 210 covalently bonded to electron bandgap mediator 207 and that forms Zwitterionic member 209 with an atom in electron bandgap mediator 207; and steric hinder 208 bonded to electron bandgap mediator 207 to provide steric hindrance for protection of coordinate center 210.

In an embodiment, a structure of physiologically stable fluorophore 200 is

wherein Z2 is terminal moiety 205; L is stability linker 203; Z1 is bridge moiety 204; and A is fluorescent moiety 202.

In an embodiment a structure of terminal moiety 205 includes

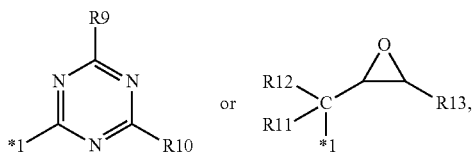

wherein *1 is a point of attachment to stability linker 203; and R9, R10, R11, R12, and R13 are independently H, an alkyl group, —OH, a halogen or a substituted alkyl group; or any of R9, R10, R11, R12, and R13, together with the atom to which they are directly attached in terminal moiety 205, forms a monocyclic ring, a bicyclic ring, or a spirocyclic ring that optionally contains a heteroatom, and is optionally substituted. In an embodiment, R9, R10, R11, R12, and R13 are independently H, —CH3, or the halogen. In an embodiment, terminal moiety 205 is

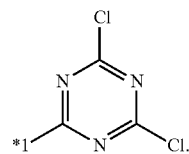

In an embodiment, a structure of stability linker 203 includes

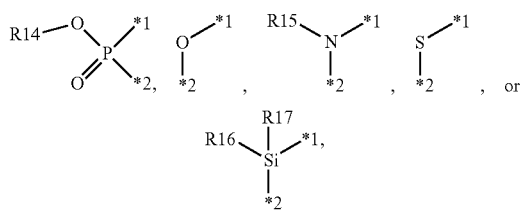

wherein *1 is a point of attachment to terminal moiety 205; *2 is a point of attachment to bridge moiety 204; and R14, R15, R16, and R17 are independently H, an alkyl group, —OH, or substituted alkyl group; or any of R14, R15, R16, and R17, together with the atom to which they are directly attached in stability linker 203, forms a monocyclic ring, a bicyclic ring, or a spirocyclic ring that optionally contains a heteroatom, and is optionally substituted. In an embodiment, R14, R15, R16, and R17 are independently H, —OH, or CH3. In an embodiment, stability linker 203 is

In an embodiment, bridge moiety 204 includes

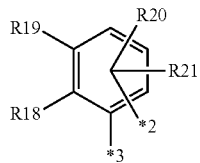 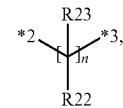 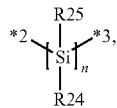

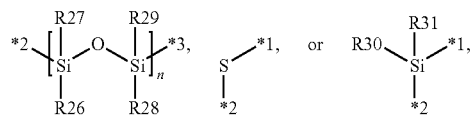

wherein *2 is a point of attachment to stability linker 203; *3 is a point of attachment to fluorescent moiety 202; and R18, R19, R20, R21, R22, R23, R24, R25, R26, R27, R28, and R29 are independently H, an alkyl group, —OH, or substituted alkyl group; or any of R18, R19, R20, R21, R22, R23, R24, R25, R26, R27, R28, and R29, together with the atom to which they are directly attached in bridge moiety 204, forms a monocyclic ring, a bicyclic ring, or a spirocyclic ring that optionally contains a heteroatom, and is optionally substituted. In an embodiment, R18, R19, R20, R21, R22, R23, R24, R25, R26, R27, R28, and R29 are independently H, —OH, or $C_3$. In an embodiment, bridge moiety 204 is

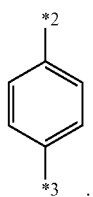

In an embodiment, a structure of fluorescent moiety 202 is

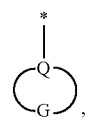

wherein Q is electron bandgap mediator 207; G is coordinate center 210; and * is a point of attachment to bridge moiety 204. Electron bandgap mediator 207 can include a conjugated electronic system that affects an electronic structure of redox moiety 201 and fluorescence emission wavelength of physiologically stable fluorophore 200. The conjugated electronic system of electron bandgap mediator 207 can include alternating multiple bonds and single bonds, wherein the multiple bonds can include a double bond or a triple bond. Moreover, electron bandgap mediator 207 can include a cyclic ring, e.g., a monocyclic ring, a bicyclic ring, or tricyclic ring, and the like so that an extent of conjugation can be selected. In an embodiment, a structure of electron bandgap mediator 207 includes

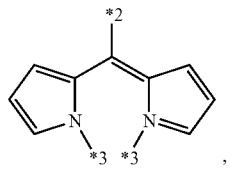

wherein *2 is a point of attachment to bridge moiety 204, and *3 are points of attachment to coordinate center 210. In an embodiment, electron bandgap mediator 207 and steric hinder 208 of fluorescent moiety 202 in combination include

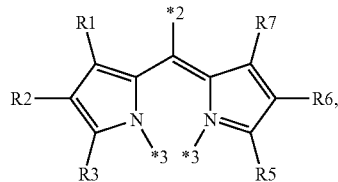

wherein *2 is a point of attachment to bridge moiety 204; *3 are points of attachment to coordinate center 210; and R1, R2, R3, R5, R6, and R7 are steric hinders 208 and are independently H, an alkyl group, alkenyl group, alkynyl group, alkoxy group, or substituted version thereof; or any of R1, R2, R3, R5, R6, and R7, together with the carbon atom to which they are attached in electron bandgap mediator 207, forms a monocyclic ring, a bicyclic ring, or a spirocyclic ring that optionally contains a heteroatom, and is optionally substituted, such that if present the monocyclic ring, the bicyclic ring, or the spirocyclic ring optionally extends conjugation of electron bandgap mediator 207. In an embodiment, steric hinder 208 comprises an alkyl group that can be substituted. In an embodiment, electron bandgap mediator 207 and steric hinder 208 of fluorescent moiety 202 in combination includes

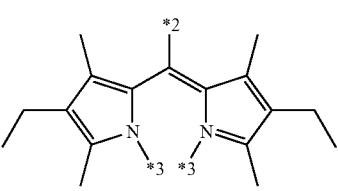

In an embodiment, coordinate center 210 includes boron. The boron is coordinated to electron bandgap mediator 207 at attachment points *3. Atoms external to electron bandgap mediator 207 can be bonded to the boron and can include a halogen such as fluorine. Accordingly, in an embodiment, electron bandgap mediator 207, steric hinder 208, and coordinate center 210 of fluorescent moiety 202 in combination include

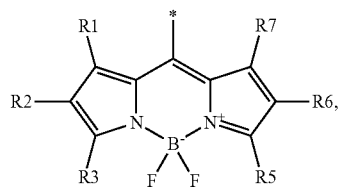

wherein * is a point of attachment to bridge moiety 204; and R1, R2, R3, R5, R6, and R7 are independently H, an alkyl group, alkenyl group, alkynyl group, alkoxy group, or substituted version thereof; or any of R1, R2, R3, R5, R6, and R7, together with the carbon atom to which they are attached, forms a monocyclic ring, a bicyclic ring, or a spirocyclic ring that optionally contains a heteroatom, and is optionally substituted, such that if present the monocyclic ring, the bicyclic ring, or the spirocyclic ring optionally extends conjugation of electron bandgap mediator 207. In an embodiment, fluorescent moiety 202 is

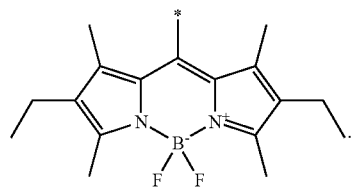 [SMILES: *C1=C2C(C)=C(CC)C(C)=[N+]2[B-](F)(F)n2c(C)c(CC)c(C)c21]

In an embodiment, physiologically stable fluorophore 200 is

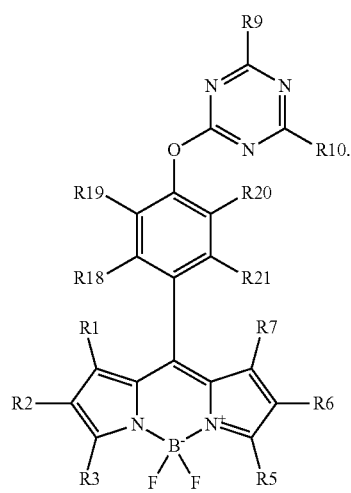

In an embodiment, physiologically stable fluorophore 200 is

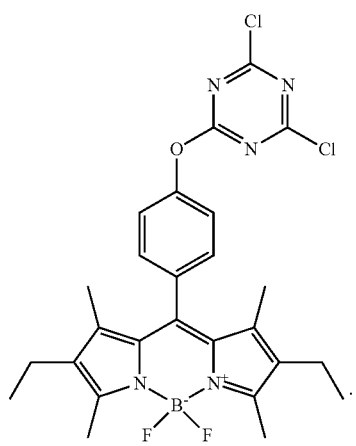 [SMILES: CCC1=C(C)C2=C(c3ccc(Oc4nc(Cl)nc(Cl)n4)cc3)c3c(C)c(CC)c(C)n3[B-](F)(F)[N+]2=C1C]

Figure 5:
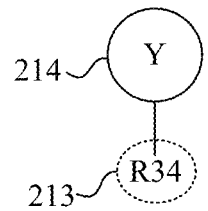
FIG. 5 shows structures of a substrate.
Figure 5:
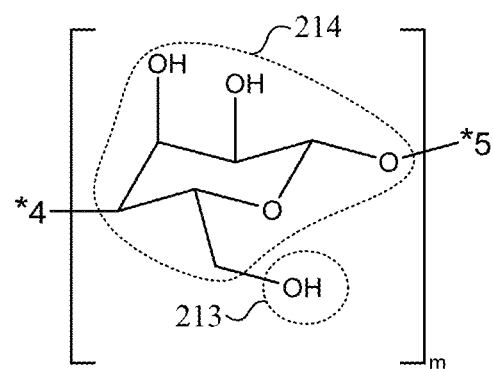
Figure 5:
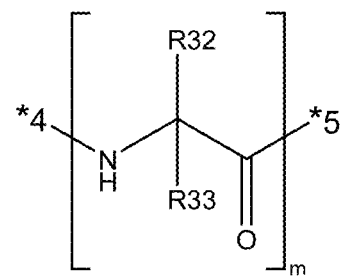
Figure 6:
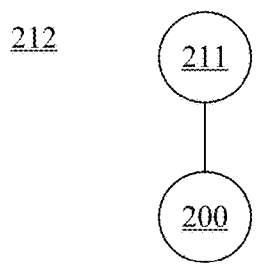
FIG. 6 shows structures of a fluorophore-substrate complex.
Figure 6:
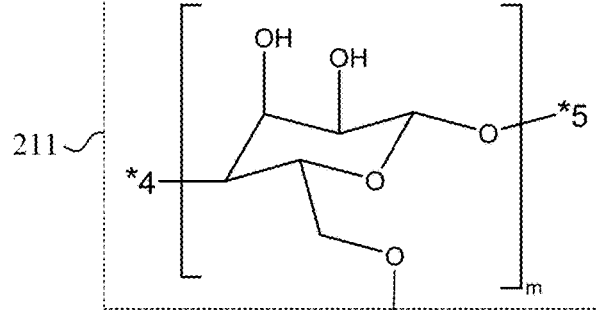
Figure 6:
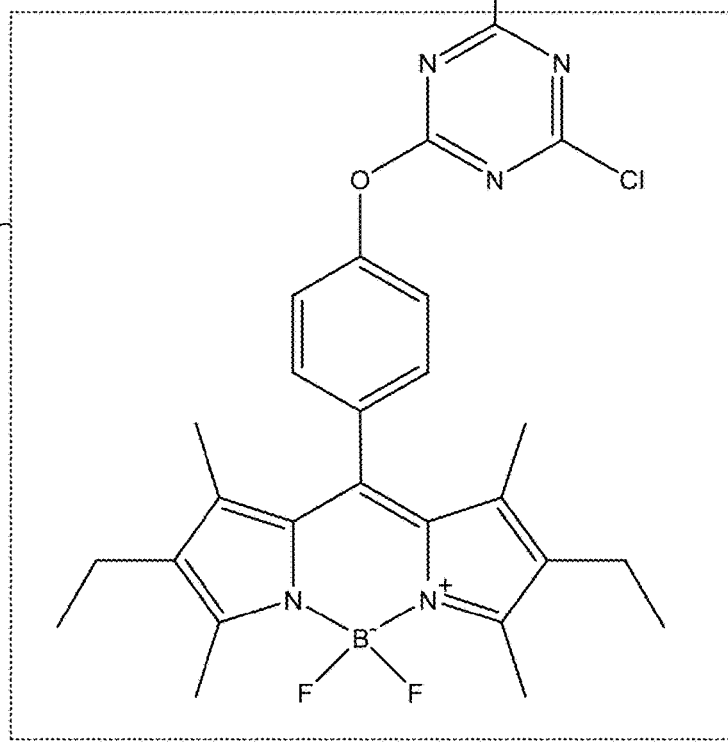
Figure 7:
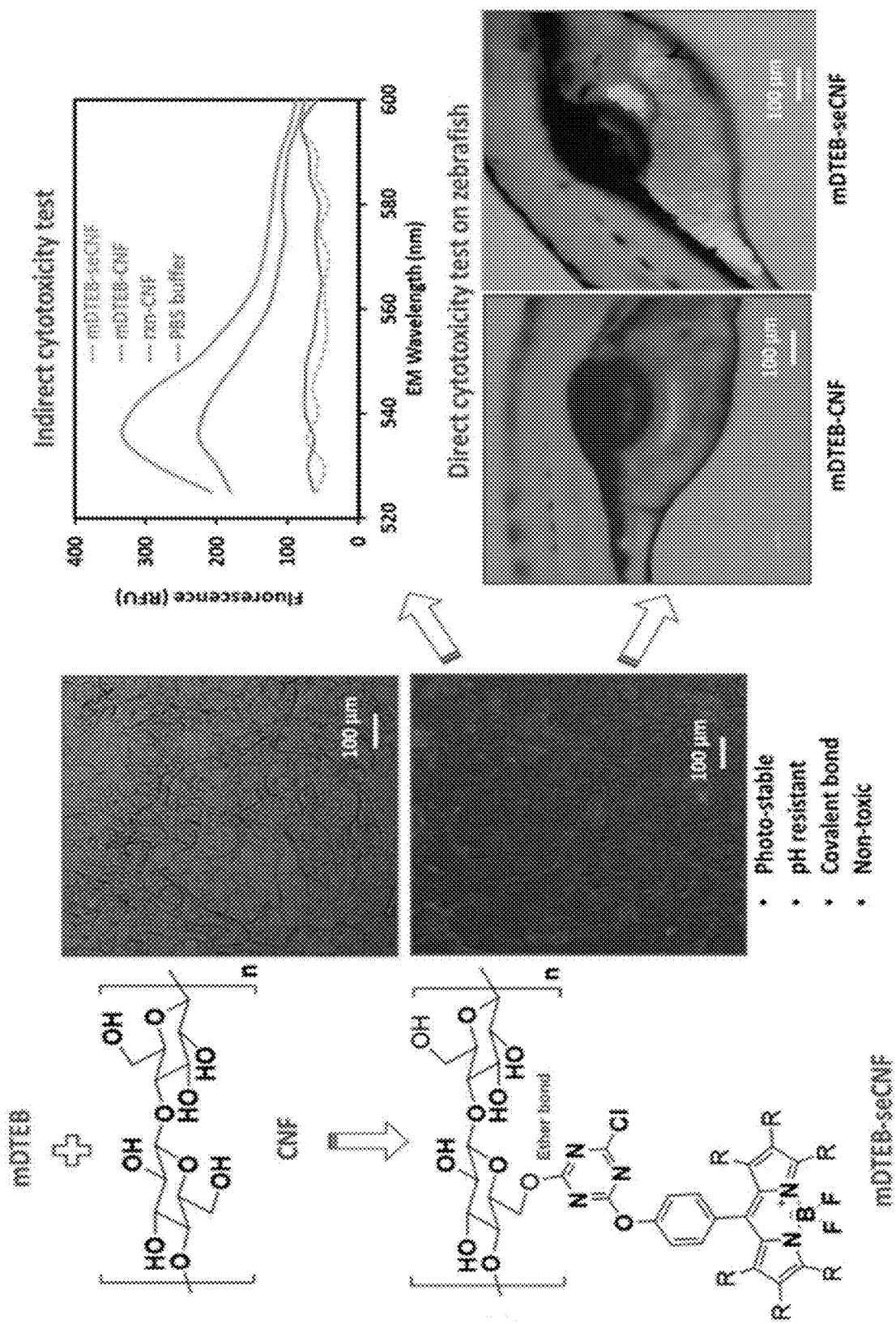
FIG. 7 shows preparation of mDTEB-labeled CNF and in vivo and in vitro cytotoxicity testing results.

In an embodiment, with reference to FIG. 5, FIG. 6, and FIG. 7, physiologically stable fluorophore 200 reacts with substrate 211 to form fluorophore-substrate complex 212. According to an embodiment, a structure of substrate 211 is Y—R34, wherein Y is basal member 214, and R34 is reactive group 213 that reacts with terminal reactive site 206 of physiologically stable fluorophore 200 and can be, e.g., a sulfate, carboxylate, phosphate, metal oxide, —OH, and the like. In an embodiment, substrate 211 is a carbohydrate, protein, particle, or polymer with a nucleophilic center, and the like. Exemplary substrates are molecules such as those found in the digestive tract of a mammal, e.g., a human. Exemplary carbohydrates are sugars, including monosaccharides, disaccharides, trisaccharides, or higher polysaccharides, and the like, such as the structure

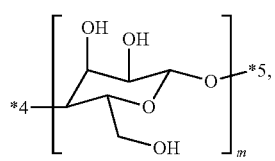

wherein m is a number of repeated monomers enclosed in square brackets, *4 and *5 are points of attachment to the next monomer or termination of the carbohydrate with a group such as H, —OH, —CH$_2$OH, and the like. It is contemplated that the carbohydrate can be derivatized to include a functional group other than —OH such as an amine group. Exemplary proteins include naturally occurring amino acids that can be the native species or derivatized, or non-naturally occurring amino acids, i.e., not synthesized by a human under normal physiological conditions, and can include the structure

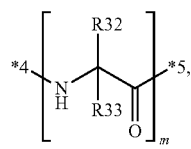

wherein m is a number of repeated monomers enclosed in square brackets, *4 and *5 are points of attachment to the next monomer or termination of the protein with a group such as H, —OH, —CH$_2$OH, —COOH, and the like. Fluorophore-substrate complex 212 can include structures such as

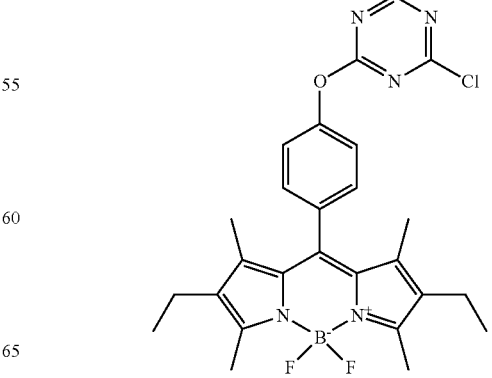

or any of physiologically stable fluorophore 200 described herein covalently bonded to any of the substrate 211 described herein.

In an embodiment, fluorophore 200 is dissolved in an aprotoic solvent prior to reaction with the substrate to form a composition. The composition is added in a selected ratio to a solution under agitation containing the substrate having the active nucleophile. This solution can be agitated, e.g., stirred, for a period, e.g., at least 6 hours. For a dilute concentration of reactants, the reaction can proceed for a longer duration.

Where a compound exists in various tautomeric forms, physiologically stable fluorophore 200 is not limited to any one of the specific tautomers, but rather includes all tautomeric forms.

Physiologically stable fluorophore 200 is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g., L, Z1, Z2, A, R1, R2, R3, R5, R7, R10, and the like. Unless otherwise specified, each variable within such a formula is defined independently of other variables. Thus, if a group is said to be substituted, e.g. with 0-2 R*, then said group may be substituted with up to two R* groups and R* at each occurrence is selected independently from the definition of R*. Also, combinations of substituents or variables are permissible only if such combinations result in stable compounds. When a group is substituted by an "oxo" substituent, a carbonyl bond replaces two hydrogen atoms on a carbon. An "oxo" substituent on an aromatic group or heteroaromatic group destroys the aromatic character of that group, e.g. a pyridyl substituted with oxo is a pyridone.

The term "substituted," as used herein, means that any one or more hydrogens on the designated atom or group is replaced with a selection from the indicated group, provided that the designated atom's normal valence is not exceeded. When a substituent is oxo (i.e., =O), then two hydrogens on the atom are replaced. Combinations of substituents or variables are permissible only if such combinations result in stable compounds or useful synthetic intermediates. A stable compound or stable structure is meant to imply a compound that is sufficiently robust to survive isolation from a reaction mixture, and subsequent formulation into physiologically stable fluorophore 200. Unless otherwise specified, substituents are named into the core structure. For example, it is to be understood that when (cycloalkyl)alkyl is listed as a possible substituent the point of attachment of this substituent to the core structure is in the alkyl portion.

The exception to naming substituents into the ring is when the substituent is listed with a dash ("-") or double bond ("=") that is not between two letters or symbols. In that case the dash or double bond symbol is used to indicate a point of attachment for a substituent. For example, —CONH$_2$ is attached through the carbon atom.

As used herein, "alkyl" is intended to include both branched and straight-chain saturated aliphatic hydrocarbon groups, having the specified number of carbon atoms. Thus, the term $C_1$-$C_6$ alkyl as used herein includes alkyl groups having from 1 to about 6 carbon atoms. When $C_0$-$C_n$ alkyl is used herein in conjunction with another group, for example, (aryl)$C_0$-$C_4$ alkyl, the indicated group, in this case aryl, is either directly bound by a single covalent bond ($C_0$), or attached by an alkyl chain having the specified number of carbon atoms, in this case from 1 to about 4 carbon atoms. Examples of alkyl include, but are not limited to, methyl, ethyl, n-propyl, isopropyl, n-butyl, t-butyl, n-pentyl, and sec-pentyl.

"Alkenyl" as used herein, indicates a hydrocarbon chain of either a straight or branched configuration having one or more carbon-carbon double bond bonds, which may occur at any stable point along the chain. Examples of alkenyl groups include ethenyl and propenyl.

"Alkynyl" as used herein, indicates a hydrocarbon chain of either a straight or branched configuration having one or more triple carbon-carbon bonds that may occur in any stable point along the chain, such as ethynyl and propynyl.

"Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

As used herein, the term "aryl" indicates aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Such substitution may include fusion to a 5- to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl.

"Cycloatkyl," as used herein, indicates a saturated hydrocarbon ring group, having only carbon ring atoms and having the specified number of carbon atoms, usually from 3 to about 8 ring carbon atoms, or from 3 to about 7 carbon atoms. Examples of cycloalkyl groups include cyclopropyl, cyclobutyl, cyclopentyl, or cyclohexyl as well as bridged or caged saturated ring groups such as norborane or adamantane. Examples of (cycloalkyl)alkyl include, but are not limited to, cyclopropylmethyl, cyclohexylmethyl, cyclohexylpropenyl, and cyclopentylethyoxy.

"Cycloalkenyl" as used herein, indicates an unsaturated, but not aromatic, hydrocarbon ring having at least one carbon-carbon double bond. Cycloalkenyl groups contain from 4 to about 8 carbon atoms, usually from 4 to about 7 carbon atoms. Examples include cyclohexenyl and cyclobutenyl. Examples of (cycloalkenyl)alkyl include, but are not limited to, cyclobutenylmethyl, cyclohexenylmethyl, and cyclohexylpropenyl.

"Haloalkyl" indicates both branched and straight-chain saturated aliphatic hydrocarbon groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Halo" or "halogen" as used herein refers to fluoro, chloro, bromo, or iodo.

As used herein, "heteroaryl" indicates a stable 5- to 7-membered monocyclic or 7- to 10-membered bicyclic heterocyclic ring which contains at least 1 aromatic ring that contains from 1 to 4, or preferably from 1 to 3, heteroatoms chosen from N, O, and S, with remaining ring atoms being carbon. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the heteroaryl group is not more than 1. A nitrogen atom in a heteroaryl group may optionally be quaternized. When indicated, such heteroaryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a [1,3]dioxolo[4,5-c]pyridyl group. Examples of heteroaryl groups include, but are not limited to, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, and 5,6,7,8-tetrahydroisoquinoline.

The term "heterocycloalkyl" indicates a saturated cyclic group containing from 1 to about 3 heteroatoms chosen from N, O, and S, with remaining ring atoms being carbon. Heterocycloalkyl groups have from 3 to about 8 ring atoms, and more typically have from 5 to 7 ring atoms. Examples of heterocycloalkyl groups include morpholinyl, piperazinyl, piperidinyl, and pyrrolidinyl groups. A nitrogen in a heterocycloalkyl group may optionally be quaternized. An "N-linked heterocycloalkyl" group is attached to the group it substitutes via a ring nitrogen.

"Heterocycloalkenyl" as used herein, indicates an unsaturated, but not aromatic, hydrocarbon ring having at least one carbon-carbon double bond. Heterocycloalkenyl groups contain from 4 to about 8 ring atoms, usually from 4 to about 7 ring atoms in which 1 to 3 ring atoms are chosen from N, O, and S, with remaining ring atoms being carbon.

The term "heterocyclic group" indicates a 5-6 membered saturated, partially unsaturated, or aromatic ring containing from 1 to about 4 heteroatoms chosen from N, O, and S, with remaining ring atoms being carbon or a 7-10 membered bicyclic saturated, partially unsaturated, or aromatic heterocylic ring system containing at least 1 heteroatom in the two ring system chosen from N, O, and S and containing up to about 4 heteroatoms independently chosen from N, O, and S in each ring of the two ring system. Unless otherwise indicated, the heterocyclic ring may be attached to its pendant group at any heteroatom or carbon atom that results in a stable structure. When indicated the heterocyclic rings described herein may be substituted on carbon or on a nitrogen atom if the resulting compound is stable. A nitrogen atom in the heterocycle may optionally be quaternized. It is preferred that the total number of heteroatoms in a heterocyclic group is not more than 4 and that the total number of S and O atoms in a heterocyclic group is not more than 2, more preferably not more than 1. Examples of heterocyclic groups include, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, dihydroisoindolyl, 5,6,7,8-tetrahydroisoquinoline, pyridinyl, pyrimidinyl, furanyl, thienyl, pyrrolyl, pyrazolyl, pyrrolidinyl, morpholinyl, piperazinyl, piperidinyl, and pyrrolidinyl.

Additional examples of heterocyclic groups include, but are not limited to, phthalazinyl, oxazolyl, indolizinyl, indazolyl, benzothiazolyl, benzimidazolyl, benzofuranyl, benzoisoxolyl, dihydro-benzodioxinyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanonyl, chromanyl, tetrahydroisoquinolinyl, isoindolinyl, isobenzotetrahydrofiiranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, 5 pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromanyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrirnidinyl N-oxide, pyridazinyl N-oxide, pyrazinyl N-oxide, quinolinyl N-oxide, indolyl N-oxide, indolinyl N oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N oxide, indazolyl N-oxide, benzothiazolyl N-oxide, benzimidazolyl N-oxide, pyrrolyl N-oxide, oxadiazolyl N-oxide, thiadiazolyl N-oxide, tetrazolyl N-oxide, benzothiopyranyl S-oxide, and benzothiopyranyl S,S-dioxide.

In physiologically stable fluorophore 200, "monocyclic ring," "bicyclic ring," or "spirocyclic ring" independently can include a heteroatom in such ring, aryl, cycloalkyl, cycloalkenyl, heteroaryl, heterocycloalkyl, heterocycloalkenyl; or can be substituted with an alkyl, alkenyl, alkynyl, alkoxy, aryl, haloalkyl, halo, or heterocyclic group.

Compounds of physiologically stable fluorophore 200 can be prepared according to methods well-known to those skilled in the art of organic chemical synthesis. The starting materials used in preparing the compounds of the invention are known, made by known methods, or are commercially available.

It is recognized that the skilled artisan in the art of organic chemistry can readily carry out standard manipulations of organic compounds without further direction.

The skilled artisan will readily appreciate that certain reactions are best carried out when other functionalities are masked or protected in the compound, thus increasing the yield of the reaction or avoiding any undesirable side reactions. Often, the skilled artisan uses protecting groups to accomplish such increased yields or to avoid the undesired reactions. These reactions are found in the literature and are also well within the scope of the skilled artisan.

Compounds of physiologically stable fluorophore 200 can have a chiral center. As a result, one may selectively prepare one optical isomer, including diastereomers and enantiomers, over another, e.g., by chiral starting materials, catalysts or solvents, or can prepare both stereoisomers or both optical isomers, including diastereomers and enantiomers at once (a racemic mixture). Since compounds of physiologically stable fluorophore 200 can exist as racemic mixtures, mixtures of optical isomers, including diastereomers and enantiomers, or stereoisomers can be separated using known methods, such as through the use of, e.g., chiral salts and chiral chromatography.

In addition, it is recognized that one optical isomer, including a diastereomer and enantiomer, or a stereoisomer, can have favorable properties over the other. When a racemic mixture is discussed herein, it is clearly contemplated to include both optical isomers, including diastereomers and enantiomers, or one stereoisomer substantially free of the other.

Compounds of physiologically stable fluorophore 200 also include all energetically accessible conformational and torsional isomers of the compounds disclosed.

Physiologically stable fluorophore 200 can be made in various ways. In an embodiment, a process for making 4-(2,8-diethyl-5,5-difluoro-1,3,7,9-tetramethyl-5H-4l4,5l4-dipyrrolo[1,2-c:2',1'-f][1,3,2]diazaborinin-10-yl)phenol (PPB) includes: dissolving 4-hydroxy benzaldehyde and 3-ethyl-2,4-dimethylpyrrole in methylene chloride under a nitrogen atmosphere; adding trifluoroacetic acid to the reaction; stirring for a selected period such as for 1.5 hours, wherein thin layer chromatography (TLC) confirms aldehyde consumption; dissolving 2,3-dichloro-5,6-dicyano-1,4-benzoquinone (DDQ) in methylene chloride and added such to the solution, e.g., through a purged syringe; stirring reaction composition for 1 hour; cooling the reaction composition by disposing the reaction flask into an ice bath to achieve a temperature of 0° C.; dropwise adding diisopropylethylamine with a purged syringe; stirring the reaction for 0.5 h; dropwise adding boron trifluoride etherate with a syringe while cooling the reaction composition to produce an exotherm; stirring the reaction for 10 hours; dispersing the reaction mixture in methylene chloride and washing it with saturated aqueous sodium bicarbonate, followed by washing with deionized water; drying the organic layer over anhydrous sodium sulfate; and isolating the PPB via column chromatography as a red solid with silica gel as a stationary phase and chloroform with ethyl acetate and hexanes solvent as a mobile phase for a 25% yield of PPB. The product was subjected to structural determination via proton nuclear magnetic resonance ($^1$HNMR) and produced the following chemical shifts δ (ppm) in CDCl$_3$: 7.1 (m, 2H, aromatic), 6.9 (m, 2H, aromatic), 2.5 (3H, S, CH$_3$), 2.3 (4H, q, CH$_2$), 2.2 (3H, S, CH$_3$), 1.3 (9H, S, CH$_3$), and 1.0 (3H, t, CH$_3$). A mass spectrum of the product provided a parent peak (+M) at 396.4 atomic mass units.

In an embodiment, a process for making 10-(4-(3,5-dichlorophenoxy)phenyl)-2,8-diethyl-5,5-difluoro-1,3,7,9-tetramethyl-5H-4l4,5l4-dipyrrolo[1,2-c:2',1'-f][1,3,2]diazaborinine (mDTEB) as physiologically stable fluorophore 200 from PPB includes: disposing PPB and potassium carbonate in dry THF in a two-necked round bottom flask under an argon atmosphere; cooling the reaction composition by disposing the flask in an ice bath stirring for 30 minutes; dissolving cyuranic chloride in dry THF and adding this composition to the reaction composition in the flask with a purged syringe dropwise; stirring the reaction composition for 10 hours to form mDTEB; and isolating mDTEB by column chromatography using acidic alumina as a stationary phase and hexanes/ethylacetate as a mobile phase. The structure of mDTEB was confirmed by $^1$NMR and produced the following chemical shifts δ (ppm) in CDCl$_3$: 7.2 (m, 2H, aromatic), 6.6 (m, 2H, aromatic), 2.5 (3H, S, CH3), 2.3 (4H, q, CH2), 2.2 (3H, S, CH3), 1.3 (9H, S, CH3), 1.0 (3H, t, CH3).

Addition of a protecting group to the alcohol on the phenol aldehyde prior to reaction with the pyrrole provides physiologically stable fluorophore 200 that is synthesized by removing the protecting group and reacting the phenol moiety with cyuranic chloride. As a result, mDTEB is produced in greater yield.

Without wishing to be bound by theory, it is believed that the process for making mDTEB can include isolating a dipyrrin core prior to reaction with borontrifluoride etherate and additionally purifying the product. This part of the process can be combined with immediate prior protection pathway to provide higher yield.

In an embodiment, a process for performing fluorescence probing includes preparing the substrate by chemically reacting it with physiologically stable fluorophore 200. Using a dry aprotic solvent, a determined amount of physiologically stable fluorophore 200 is dissolved to prevent formation of dimers. The substrate is dissolved or dispersed in a similar solvent and stirred at room temperature. The reaction can be performed in anhydrous conditions, such as a glove box or Schlenk line setup. The solution containing physiologically stable fluorophore 200 can be added to the solution containing the substrate. This resulting solution can be stirred for at least 6 h. If the concentrations are very dilute, longer reaction times can be used. After the reaction, the substrate can be washed, which can include flash chromatography, dialysis, tangential flow filtration, or centrifugation followed by redispersion cycles. The process for fluorescence probing can depend upon the substrate being tracked. For solid substrates, plate readers, fluorimeters equipped with a solid sample holder, and fluorescent microscopes can be used. A light source for excitation with a wavelength of 516 nm can be used. Wavelengths from 488 nm to 520 nm can be used. Solution-based substrates can be examined using similar equipment. The excitation source can remain the same.

Physiologically stable fluorophore 200 and processes herein have numerous advantageous and unexpected benefits and uses. In an embodiment, a process for It should be appreciated that physiologically stable fluorophore 200 and performing fluorescence probing can be used for toxicity studies, particle tracking, and imaging.

It is contemplated that physiologically stable fluorophore 200 is a fluorescent molecule with fluorescent moiety 202 as an inert, fluorescent center and terminal reactive site 206 as a chemical handle that reacts with alcohols or amines forming an ether type of bond in fluorophore-substrate complex 212. With regard to molecular design, fluorescent moiety 202 can be, e.g., 2,8-diethyl-5,5-difluoro-1,3,7,9,10-pentamethyl-5H-4λ$^4$, 4λ$^4$-dipyrrolo[1,2-c:2',1'-f][1,3,2]diazaborinine (Bodipy). The Bodipy structure provides photo stability and is non-toxic. A moiety in the meso position of the fluorescent center can be functionalized with chlorotriazine. This functional group reacts with nucleophiles such as alcohols or amines under mildly basic conditions to yield a stable aromatic ether linkage in fluorophore-substrate complex 212, wherein this bond is resistant to pH and enzymatic attack, which sets it apart from conventional amide or thiourea bonds found in conventional fluorescent dyes. In addition, the 2-position and 8-position of fluorophore-substrate complex 212 are sterically protected with hydrophobic groups so that the electrophilic center is inert with regard to chemical reactivity, e.g., in the digestive tract. The photophysical characteristics of physiologically stable fluorophore 200 such as 10-(4-((4,6-dichloro-1,3,5-triazin-2-yl)oxy)phenyl)-2,8-diethyl-5,5-difluoro-1,3,7,9-tetramethyl-5H-4l4,5l4-dipyrrolo[1,2-c:2',1'-f] [1,3,2]diazaborinine (mDTEB) provides for excitation and emission bands that are amenable to excitation and detection with conventional instrumentation.

Physiologically stable fluorophore 200 and processes disclosed herein have numerous beneficial uses, including particle tracking using a similar detection method associated with radio scintillation studies, detection of otherwise trace amounts of substrates in a system, and localization of substrates in a system when combined with fluorescence microscopy. Physiologically stable fluorophore 200 does not lose its photophysical properties throughout a broad range of pH and temperatures so that it can be used for digestive studies. Advantageously, physiologically stable fluorophore 200 and performing fluorescence probing overcome limitations of technical deficiencies of conventional compositions loss or reduction in performance with changes in pH and temperature. Further, Fluorophore 200 can readily be attached to primary alcohols, which can limit conventional labeling strategies.

Conventional methods for testing or tracking nanosized or micron-sized particles involve radioactive isotopes like $^{14}C$ or conventional fluorescent dyes with pH sensitivities or labile attachment chemistries. Conventional isotopic methods can be expensive and require specialized facilities. Conventional fluorophores can be quenched either in acidic conditions pH<5 or basic conditions pH>8. Both such conditions are characteristic of the human digestive tract. Further, amides and thioureas can be attacked by digestive enzymes in addition to pH, producing free dye molecules. It is contemplated that physiologically stable fluorophore 200 such as mDTEB is a chemical label that is nontoxic and resistant to digestive process and conditions. Beneficially synthesis of physiologically stable fluorophore 200 can be accomplished in two steps so that synthesis thereof is less complex than conventional fluorescent dyes.

Physiologically stable fluorophore 200 and processes herein operate outside wavelengths typical of biological systems and reduces the amount of background interference from biological sources such as amino acids and DNA. Moreover, physiologically stable fluorophore 200 and performing fluorescence probing provide a less expensive pathway to conduct toxicity studies than conventional radio isotopic labeling.

The articles and processes herein are illustrated further by the following Examples, which are non-limiting.

EXAMPLES

Example 1. Fluorescently Labeled Cellulose Nanofibers for Environmental Health and Safety Studies An optimal methodology for locating and tracking cellulose nanofibers (CNF) in vitro and in vivo is crucial to evaluate the environmental health and safety properties of these nanomaterials. Use of a boron-dipyrromethene (BODIPY) reactive fluorescent probe, meso-DichlorotriazineEthyl BODIPY (mDTEB), selectively tailored for labeling CNF used in simulated or in vivo ingestion exposure. Time-correlated single photon counting (TCSPC) fluorescence lifetime imaging microscopy (FLIM) was used to confirm covalent attachment and purity of niDTEB labeled CNF. The photoluminescence properties of mDTEB labeled CNF, characterized using fluorescence spectroscopy, include excellent stability over a wide pH range (from pH=2 to pH=10) and high quantum yield, which provides detection at low (µM) concentrations. FLIM analysis also showed that lignin-like impurities present on the CNF reduce the fluorescence of the mDTEB labeled CNF, via quenching. Therefore, the chemical composition and the methods of CNF production affect subsequent studies. An in vitro triculture, small intestinal, epithelial model was used to assess the toxicity of ingested mDTEB labeled CNF. Zebrafish (Danio rerio) were used to assess in vivo environmental toxicity studies. No cytotoxicity was observed for CNF, or mDTEB labeled CNF, either in the triculture cells or in the zebrafish embryos.

Cellulose is an abundant renewable, biodegradable and non-toxic biopolymer on earth. As used herein, "cellulose nanomaterials" (CNM) refers to cellulosic extracts or processed materials, having defined nano-scale structural dimensions. CNM are available in the market as a commercial product and their areas of application span across the paper, paint, construction, biocomposites, electronics, tissue engineering, drug delivery, food and packaging industries. These nanoparticles exhibit exceptional features such as nano morphology in at least two dimensions, high aspect ratios, large surface areas, low densities, tunable surface functionalities and unique rheologies. CNM exhibit biodegradability, biocompatibility, and abundance of hydroxyl groups, which are easily modified by the grafting of different molecules. However, owing to the nanoscale features, environmental health and safety (EHS) of CNM is an issue to be assessed.

CNM are classified into two major groups: cellulose nanocrystals (CNC), and cellulose nanofibrils (CNF). Variations in CNM generally arise from three factors: (i) the cellulose source (wood, tunicates, bacteria) (ii) extraction/production method (pretreatments step) and (iii) surface chemistry (functionalization). CNM extracted from plants are prepared by a variety of pretreatment steps followed by various refinement steps. Refinement by acid hydrolysis of the cellulose fibers preferentially cleaves the chains at the disordered regions of the cellulose and gives rod-shaped crystals, CNC, with dimensions of 2 nm to 20 nm diameters and 100 nm to 500 nm lengths. The CNC contain highly crystalline cellulose domains, ranging from 54% to 88% crystallinity. In contrast, refinement by mechanical treatments uses high shear forces to comminute the cellulose source material into CNM, and the resulting particles are designated as either microfibrillated cellulose (MFC), nanofibrillated cellulose (NFC), or cellulose nanofibers (CNF), depending on the fibrillation extent. MFC and NFC both contain significant amounts of micron sized particles (in at least 2 dimensions) and are not a part of this study. CNF exhibit the highest extent of fibrillation and are micrometer long fibrils with diameters on the nanometer scale (typically <50 nm) that contain both amorphous and crystalline cellulose domains. These fibrils exhibit large specific surface areas, extensive hydrogen bonding between fibrils, and a high degree of entanglement. This gives rise to highly viscous aqueous suspensions at relatively low concentrations (below 1 wt. %). CNF also contain trace amounts of lignin, hemicellulose, or fragments of these contaminants.

Environmental and health impacts of CNF can be studied. Increased interest in commercialization has prompted progress towards characterizing the human and environmental safety (EHS) of CNF, both in the workplace and in potential products. The potential use of CNF in medical, food, and packaging applications also requires examination of EHS by ingestion. Some of the potential implications of CNF ingestion exposures have recently been studied and reported in the literature. These studies have included investigations of the toxicity of physiologically-relevant pre-digested CNF in an in vitro model of the small intestinal epithelium, as well as in vivo systemic toxicity, intestinal epithelial health effects, and impacts on the gut microbiota in rats. Toxicology results are predominantly negative without significant adverse effects reported. One study, however, remains elusive: the measurement and reporting of the absorption, distribution, metabolism, and excretion (ADME), or i.e., the toxicokinetic characteristics, of CNF, which is for demonstrating the safety of oral exposure. Such studies involve accurately quantifying CNF in biological media in order to determine ADME by combined direct measurements and mass balance calculations.

A protocol for studying the safety of carbohydrates is radioactive carbon ($^{14}C$) labeling and tracing. The $^{14}C$ traces are then detected and quantified in various organs of an exposed rodent test model to establish toxicokinetic profiles, which are then used in physiologically-based toxicokinetic models to assess safety. However, the use of radioactive carbon is dangerous to occupational workers and the amount of $^{14}C$ within a test substance is miniscule. This requires highly specialized instrumental resources (personnel and facilities), which are often cost-prohibitive. Fluorescent labeling is a viable alternative safety testing strategy that should be further advanced and used in iterative product development.

Fluorescence offers several advantages as a label for these types of studies: it uses a fairly simple labeling process, there are a range of fluorophores available to avoid interference, it can be used to examine interfaces, and imaging is available in most laboratories. There are some disadvantages that must be considered: pH and photo stability, detection limits, chemical stability, and interferences with biological autofluorescence. These disadvantages can be avoided by choosing the appropriate fluorophore. The requirements for an ADME test are that the material must be representative of commercial cellulose nanomaterial, the label must remain attached to CNM during digestive process, the CNM needs to be detectable at various stages of digestion, it must be detectable at high dilution (1-10 μg/mL), and the fluorophore must not have any biological fluorescence interferences. The range of appropriate fluorophores and attachment chemistries used to produce fluorescently labeled CNF for ADME studies is narrowed by these conditions. The reaction must be performed in water to avoid aggregation. The reaction steps and extent of labeling must be minimized to prevent changes in surface chemistry or surface energy. The labeling bond must not dissociate between pH 1 and pH 8 or in the presence of digestive enzymes. The fluorophore can have an emission with high quantum yield, invariable quantum yield over pH range, and an excitation $\lambda > 500$ nm. A wide variety of fluorogenic dyes have been used to label CNM. Conventional strategies fail to meet these criteria.

Described herein is a synthesis of a compound that is chemically and enzymatically stable, fluorescently labeled-CNF that meets criteria for ADME studies and to study specific cytotoxicity effects and biodistribution in vivo and in vitro after ingestion (FIG. 7). The notation used for the various materials used in this Example is listed in the Table

| Abbreviation | Material Description |
|---|---|
| mDTEB | Synthesized fluorophore, meso-DichloroTriazineEthyl BODIPY |
| CNF | Cellulose nanofibrils, as received |
| seCNF | Surface extracted CNF |
| mDTEB-CNF | mDTEB labeled as received CNF |
| mDTEB-seCNF | mDTEB labeled surface extracted CNF |
| rxn-CNF | As received CNF exposed to reaction conditions without presence of mDTEB |
| rxn-seCNF | Surface extracted CNF exposed to reaction conditions without presence of mDTEB |

With regard to materials, cellulose nanofibers (3.0% by mass, never-dried) was used. Boron-dipyrromethene (BODIPY) fluorescent probe and meso-DichloroTriazine-Ethyl BODIPY (mDTEB) were synthesized. Deionized water was used. Solvents were chromatographically pure. $Na_2CO_3$, NaOH, and buffer salts were used. The pH value of the buffer was measured with a pH meter.

With regard to physico-chemical characterization of CNF, chemical composition of CNF was analyzed according to NREL procedures and determined to include 96.0% by mass cellulose, 1.5% by mass hemicellulose and 2.5% by mass lignin. The total lignin content was determined from CNF samples according to TAPPI T222 om-06 and TAPPI UM250, to analyze the acid-insoluble residues (AIR) and acid-soluble lignin (ASL), respectively. CNF was hydrolyzed using sulfuric acid (72% by mass) for 1 h at 30° C. After hydrolysis, samples were diluted (3% by mass) in deionized water and autoclaved at 121° C. for 1 h. The resulting solutions were cooled to room temperature and the precipitates were filtered and dried. The mass of the precipitate was designated as the AIR content (also known as Klason lignin). The ASL content was calculated by measuring absorbance at 205 nm with a spectrophotometer. Surface impurities of CNF was examined by a confocal laser scanning microscopy (CLSM) with a 20x, 0.7 numerical aperture (NA) air objective. Additional information about the photoluminescence properties of CNF extracted impurities was obtained using fluorescence spectroscopy.

Preparation of surface extracted CNF. As received CNF (3.0% by mass) was diluted by adding 0.1 M NaOH to obtain 1.5% by mass CNF. The diluted CNF suspension was autoclaved at 105° C. for 15 min and centrifuged at 520 rad/s (12,500×g) for 10 min to separate solid and liquid fractions. Analysis of the liquid fraction was performed using a fluorimeter. The solid fraction was washed with water until a neutral pH was reached. Cleaned, extracted CNF with a final concentration between 2.5% and 4% by mass was designated as surface extracted CNF (seCNF) and stored at 4° C. until needed for further analysis or experiments.

Synthesis of mDTEB labeled CNF. Either as received CNF slurry or seCNF slurry. (to contain 4.5 g dry mass) and 100 mL of water was added to 150 mL of 50 mM $Na_2CO_3$ and mechanically stirred for 30 min. 2 mg of mDTEB was dissolved in 500 μL of acetone, then added to the alkaline CNF suspension and stirred for 72 h in the dark at room temperature. When the reaction was complete, the modified CNF was isolated by centrifugation at 520 rad/s (12,500×g) for 20 min. After centrifugation, the excess of mDTEB was removed by washing the labeled CNF with an ethyl acetate—water mixture (washing solvent). Purification was carried out at 150 rad/s for 10 min followed by centrifugation at 420 rad/s (10,000×g) for 10 min. The purification step was repeated until no fluorescent signal was detected in the washing liquor. The labeled CNF was resuspended in water and centrifuged repeatedly until the ethyl acetate was removed. Cleaned, labeled CNF was stored at 4° C. until needed for the further analysis.

With regard to assessment of photoluminescence properties of labeled CNF, photoluminescence excitation (PLE) spectroscopy maps and line scans were obtained with spectrofluorometer and corrected for the instrument's source spectral distribution and detector spectral response. Excitation wavelengths were scanned in 5 nm increments using a 450 W xenon lamp through a 2 nm slit. Emitted light was collected at 90° and measured using a liquid N2-cooled InGaAs detector over 2 nm increments through a 2 nm slit. The fluorescence emission spectra of mDTEB-CNF and mDTEB-seCNF were created using an excitation wavelength ($\lambda_{Ex}$) of 514 nm with emission wavelengths from 530 nm to 650 nm. An excitation plot was created with an emission wavelength ($\lambda_{Em}$) of 540 nm with excitation wavelengths from 400 nm to 530 nm. The UV-Vis absorption spectra were collected with a UV-Vis-NIR spectrophotometer. The pH stability of mDTEB-CNF and mDTEB-seCNF were evaluated by measuring fluorescence intensity using a Nanolog-3 spectrofluorometer. Buffered solutions containing 0.5 mg/mL labeled CNF in the range of pH 2 to 10 were equilibrated to 37° C., and the fluorescence intensity was measured at $\lambda_{Em}$ 540 nm. Thermal stability of mDTEB-CNF and mDTEB-seCNF were studied by autoclaving 0.5 mg/mL labeled CNF in an alkaline solution (0.1M NaOH) at 105° C. for 15 min. Unlabeled materials suspended at the same concentration in the same solutions were used as controls. The photoluminescence spectra of autoclaved washed fibers, the collected supernatants, and the controls were recorded using the spectrofluorometer as described above. The concentration-dependence of the labeled CNF fluorescence was assessed by measuring the fluorescence intensity of labeled CNF diluted to concentrations between 2 µg/mL and 2 mg/mL using PBS buffer or deionized water. Fluorescence intensity was recorded on a multimode microplate reader equipped with monochromator optics at $\lambda_{Ex}$ 514 nm and $\lambda_{Em}$ 540 nm. Measurements were performed with top well illumination, using black/clear bottom 96-well micro-plates. Each suspension was measured in triplicate using 200 µL samples. Intensity values were background corrected. For fluorescence images, dilute labeled CNF suspensions were deposited onto an ultraviolet ozone (UVO)-treated glass slides and dried at room temperature. Confocal microscopy measurements were carried out using an upright microscope with a 20×, 0.7 numerical aperture (NA) air objective. Images were acquired by exciting at 488 nm and collecting emission at 500 nm to 650 nm.

With regard to microscopy images of CNF, the fluorescence lifetime imaging microscopy (FLIM) of CNF samples were determined using a time-resolved single photon counting module (SPCM) set up. CNF samples were drop-cast onto ultraviolet ozone (UVO)-treated glass slides, dried at room temperature, and imaged using two-photon fluorescence. The images presented are 256×256 pixels with dwell times of a 2 ms. Wide-field optical microscopy images were collected using an inverted microscope. Samples were diluted to 0.1% by mass and 1 drop was placed on glass microscope slide. The sample was spread and allowed to air dry before imaging in bright-field mode. Scanning electron microscopy (SEM) images of CNF were obtained on a focused ion beam scanning electron microscope with an acceleration voltage of 5.00 kV using either an ETD or ICE detector. Samples were prepared by first drying an aliquot of suspended cellulose on an SEM puck and pin stub. The sample was then sputter coated with a 5 nm layer of carbon to decrease sample charging.

With regard to inverse gas chromatography (iGC), surface energy analyses were carried out using an iGC surface energy analyzer (SEA), and the data were analyzed using both standard and advanced SEA analysis software. Here, iGC surface energy measurements and analysis calculations were conducted at finite dilutions according to the published procedure. Approximately 150 mg of freeze-dried CNF was packed into individual silanized glass columns. The BET surface area was determined using a linear regression of n-octane surface coverage between 0.05 and 1.0 fractional coverage. Each column was conditioned and dried under a flow of anhydrous helium for 30 min, before n-alkane probe molecules (hexane, nonane, octane, and heptane) and polar probe molecules (acetone, ethanol, acetonitrile, ethyl acetate, and dichloromethane) were introduced over a range of injection volumes. This method was used to determine the dispersive and acid-base components of surface energy as a function of fractional surface coverage. This method also permits the investigation of energetic heterogeneity.

With regard to dynamic light scattering/zeta potential (DLS/ZP), average particle sizes and surface charges of the CNM were determined. Samples were placed in 20 mL scintillation vials and diluted to 0.1% by mass in ultrapure water. Dilutions of CNF were prepared in triplicate and measured in triplicate (9 total measurements for each material tested) using 1 mL sample suspensions dispensed in disposable microcuvettes. An absorbance of 0.01 and refractive index of 1.580 were used for CNF and a viscosity of 0.8872 cP and refractive index of 1.330 were used for the dispersant (water). DLS reports an intensity-weighted averaged hydrodynamic diameter (D50) and polydispersity index (PDI), which is a dimensionless measure of particle size heterogeneity. Because DLS can only provide accurate size measurements for nearly-spherical values, for suspensions of anisotropic materials with high aspect ratios, like CNF, D50 values indicate only relative particle sizes rather than true hydrodynamic diameters.

Endotoxin and sterility assessment of CNF materials. All CNF materials were tested for endotoxin using the recombinant factor C (rFC) assay. Here, 10 g/mL suspensions of CNFs, as well as endotoxin standard dilutions, and ENM suspensions spiked with 0.5 EU/ml endotoxin, were prepared in endotoxin-free water. Samples, spiked samples, and standard dilutions were dispensed, into a pre-warmed (37° C.) 96 well plate (100 µL/well), and mixed, with 100 µl assay reagent (8:1:1 ratio of assay buffer, enzyme, and substrate). Fluorescence ($\lambda_{Ex}$=380 nm, $\lambda_{Em}$=440 nm) was measured at t=0 min and 90 min. Endotoxin levels were calculated from sample fluorescence using a standard curve equation generated from a range of endotoxin standard dilutions.

Microbiological sterilities of all CNF materials were assessed using the WHO protocol in the international pharmacopoeia. CNF materials were suspended at 1 mg/mL, and 1 mL of each suspension was added to 10 mL of liquid thioglycolate medium at pH 6.9-7.3. The resulting solutions were incubated at 37° C. for 14 d and examined daily for indications of bacterial growth. Every three days during incubation, samples of broth were spread onto tryptic soy agar plates, and mixed with either potato dextrose agar or plate count agar to create pour plates. These plates were incubated at 37° C. for 3 days and then examined for growth of bacterial and fungal colonies.

With regard to in vitro simulated digestion, in vitro simulated digestion was performed using a 3-phase simulator. CNF were added to a fasting food model (5 mM phosphate buffer) at 0.75% or 1.5% by mass. CNF has not been approved as food additives, and therefore no guidelines for concentrations exist. Microcellulose materials are approved GRAS additives, with powdered cellulose allowed at up to 3.5% by mass, and microcrystalline cellulose at up to 3.0% by mass in some meat and poultry products. Given greater surface areas of nanocellulose materials, the high viscosity of CNF suspensions at greater than 1.0% by mass, and the reported efficacy of CNF in food applications at 0.2% to 1.0% by mass usages may exceed 1% by mass. Concentrations of 1.5% and 0.75% by mass were thus chosen to bracket this value. Food-nanomaterial mixtures were combined with equal volumes of simulated saliva fluid, and incubated for 2 minutes. The resultant mouth digesta was then combined with simulated gastric fluid and incubated for 2 h at 37° C. in an orbital shaker. The resulting gastric phase digesta was combined with additional salts, bile extract and lipase to simulate intestinal fluid, and incubated at 37° C. for 2 h while maintaining a constant pH of 7.0 using a titration device.

In vitro toxicity assessment in a tri-culture model of the small intestinal epithelium was determined by an in vitro tri-culture small intestinal epithelial model. Caco-2 and HT29-MTX cells were grown in high-glucose DMEM supplemented with 10% by mass heat-inactivated fetal bovine serum (FBS), 10 mM HEPES buffer, 100 IU/mL penicillin, 100 µg/ml streptomycin, and non-essential amino acids (1/100 dilution of 100× solution). Raji B cells were cultured in RPMI 1640 media supplemented with 10% by mass FBS, 10 mM HEPES buffer, 100 IU/mL Penicillin and 100 µg/mL Streptomycin. To prepare transwell inserts, Caco-2 and HT-29MTX cells were harvested and resuspended in DMEM at $3 \times 10^5$ cells/cm$^3$, and combined at 3:1 (Caco-2:HT29-MTX). 1.5 ml of the mixture was dispensed in the apical chamber, and 2.5 mL of complete DMEM media was added to the basolateral compartment of each transwell. Media was replaced after 4 d, and subsequently every other day, until day 15. On days 15 and 16, basolateral media was replaced with 2.5 mL of 1:1 DMEM: RPMI complete media containing a Raji B cells at $1 \times 10^6$ cells/mL. For 96-well plates, 100 µl of the 3:1 mixture of Caco-2 and HT-29MTX cells were dispensed into each well of black-walled, clear bottom plates, and media was changed after 4 d, and subsequently every other day, until day 17. Toxicology experiments were performed on day 17.

The final small intestinal phase digestas of mDTEB-seCNF and CNF were combined with DMEM in a ratio of 1:3, and the 1.5 mL (transwells) or 200 µl (96-well plates) was applied to test cells. Media in control wells was replaced with fresh complete DMEM media. Cells were incubated for 24 h. Supernatants from transwells was collected for LDH (cytotoxicity) analysis, and 96-well plates were processed for viability assessment. LDH was measured using a Pierce LDH assay kit with untreated control wells used to measure background LDH release, and lysed cells providing maximum LDH release measurements. Percent cytotoxicity was calculated from test, background and maximum LDH controls. Assessment of metabolic activity (cell viability) was performed using the PrestoBlue viability reagent. Wells were washed 3 times with 200 µL of PBS, 100 µL of 10% by mass PrestoBlue reagent was added to each well, plates were incubated at 37° C. for 15 minutes, and fluorescence was measured at $\lambda_{Ex}$=560 nm and $\lambda_{Em}$=590 nm.

With regard to assessment of in vivo Zebrafish toxicity, to determine acute in vivo toxicity and biodistribution behavior of CNF, we used an embryonic zebrafish model, as their genetic, cellular, and organ structure is similar to humans. Adult zebrafish (Danio rerio) were maintained in an aquatic research laboratory. Embryos were collected from group spawns of wild-type 5D zebrafish and staged to ensure all embryos were at the same developmental stage at the start of the experiment. Embryos were enzymatically dechorionated at 6 hours post fertilization (hpf) with pronase. At 8 hpf, embryos were incubated in batches (n=50) in 25 mL of either 1 mg/mL mDTEB-CNF, 1 mg/mL mDTEB-seCNF, or Fish Water (FW). FW was prepared by mixing 0.26 g/L Instant Ocean salts in reverse osmosis water and adjusting the pH to 7.2±0.2 with sodium bicarbonate. Conductivity was between 480 µS/cm to 520 µS/cm. At 120 hpf the zebrafish were rinsed three times with FW, then imaged by confocal microscopy ($\lambda_{Ex}$ 504 nm, $\lambda_{Em}$ 528 nm). Protoslo was added to each deep well to ensure that the fish remained still while being imaged.

The development of a reactive fluorescent label for cellulose nanomaterials for ingestion exposure studies requires careful consideration. The labeled CNM can be representative of cellulose nanomaterials, remain attached to the cellulose during the digestive process, be detectable at various stages of digestion, be detectable at high dilution (~1 µg/mL), and not subject to interference from biological fluorescence sources. As noted in the introduction, these criteria eliminate nearly every labeling chemistry used previously, including the popular use of isothiocyanates and most commercially available dyes. To meet all of the properties for digestive studies of CNM, we synthesized a new fluorophore referred to as mDTEB.

A single pot chemical reaction was performed to synthesize fluorescently labeled CNF. The BODIPY-based fluorescent probe (mDTEB) was covalently attached to CNF using an etherification reaction in the presence of sodium carbonate, resulting in an ether bond formation between the triazine moiety of mDTEB and hydroxyl group of CNF. A mDTEB probe was selected over other fluorophores, because it is pH stable, photostable, and enzymatically stable. Further, BODIPY based dyes have inherently advantageous photophysical properties, including large absorption coefficients, high fluorescence quantum yields, relative insensitivity to changes in polarity and pH value, narrow emission profiles, nanosecond excited-state lifetimes, improved photostability relative to fluorescein are available in a wide range of colors. A considerable volume of work involving BODIPY fluorophores has focused on their use as labeling reagents for biological materials.

Figure 8:
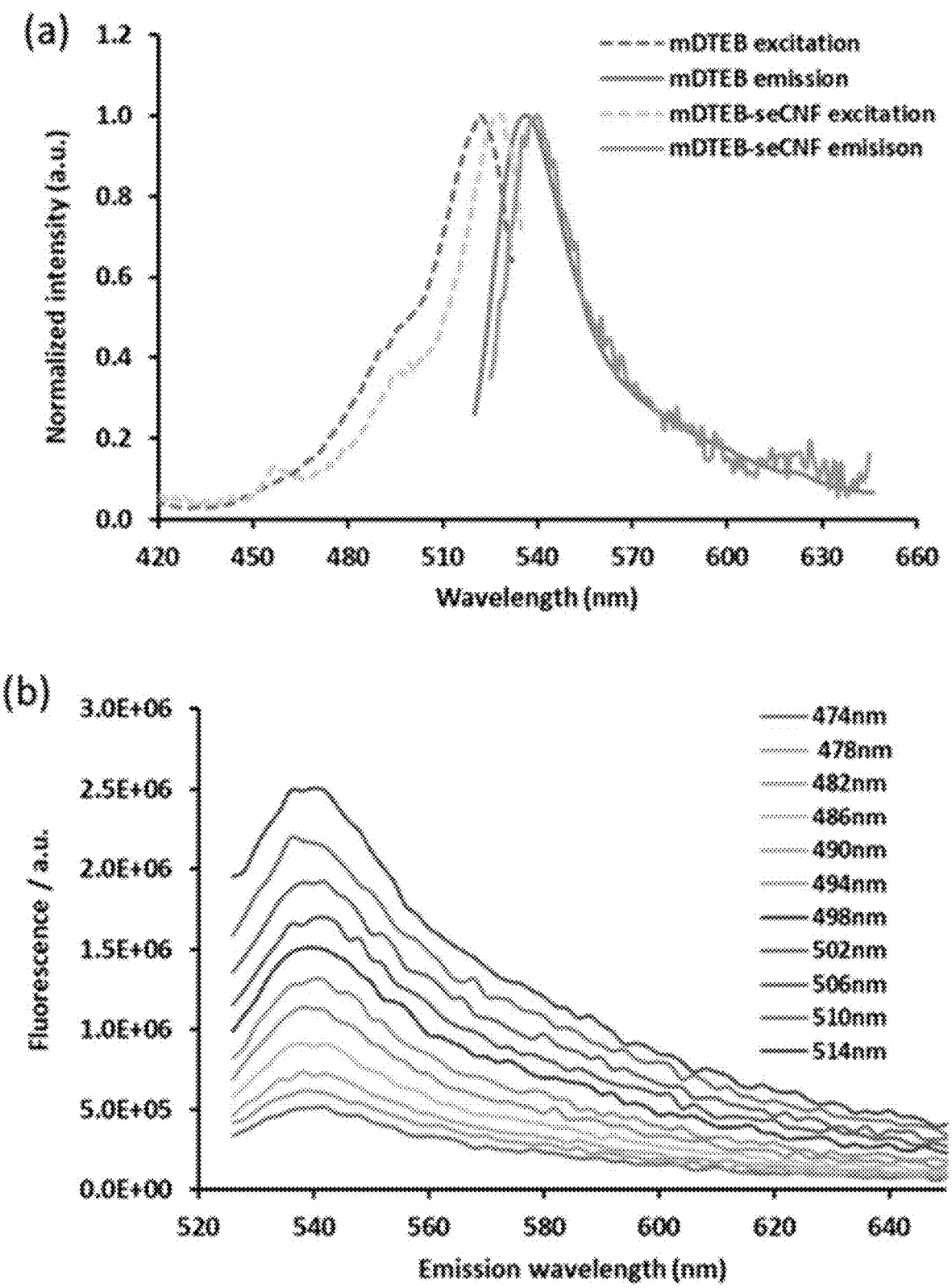
FIG. 8 shows fluorescent properties of mDTEB dye and mDTEB-seCNF: (a) normalized fluorescence spectroscopic data of mDTEB-seCNF compared with the free dye (mDTEB); and (b) photoluminescence emission spectra of mDTEB-seCNF.

Photoluminescence properties (excitation and emission spectra) of the mDTEB dye and mDTEB-seCNF were recorded using fluorescence spectroscopy. A maximum excitation intensity was obtained at wavelength of 530 nm for mDTEB-seCNF (FIG. 2a, dotted line), while the maximum emission intensity was obtained at wavelength of 540 nm (FIG. 8a, solid line). Similar excitation $\lambda_{max}$ and emission $\lambda_{max}$ were observed for mDTEB-CNF, but with lower fluorescence intensities at the same concentration of CNF (500 µg ml$^{-1}$). The small Stokes shift of 10 nm is one of the few disadvantages to using BODIPY dyes, and can limit the choice of fluorescence measuring instruments for some studies. To determine whether or not the synthesized mDTEB-seCNF exhibited excitation dependent photoluminescence, emission spectra were collected for a range of excitation wavelengths. FIG. 8b shows the photoluminescence emission spectra of mDTEB-seCNF with excitation wavelengths from 474 nm to 514 nm. These results illustrate that the mDTEB-CNF produces strong fluorescence emissions with symmetrical emission peaks and an increase in fluorescence emission as the excitation wavelength increases from 474 nm to 514 nm.

Figure 9:
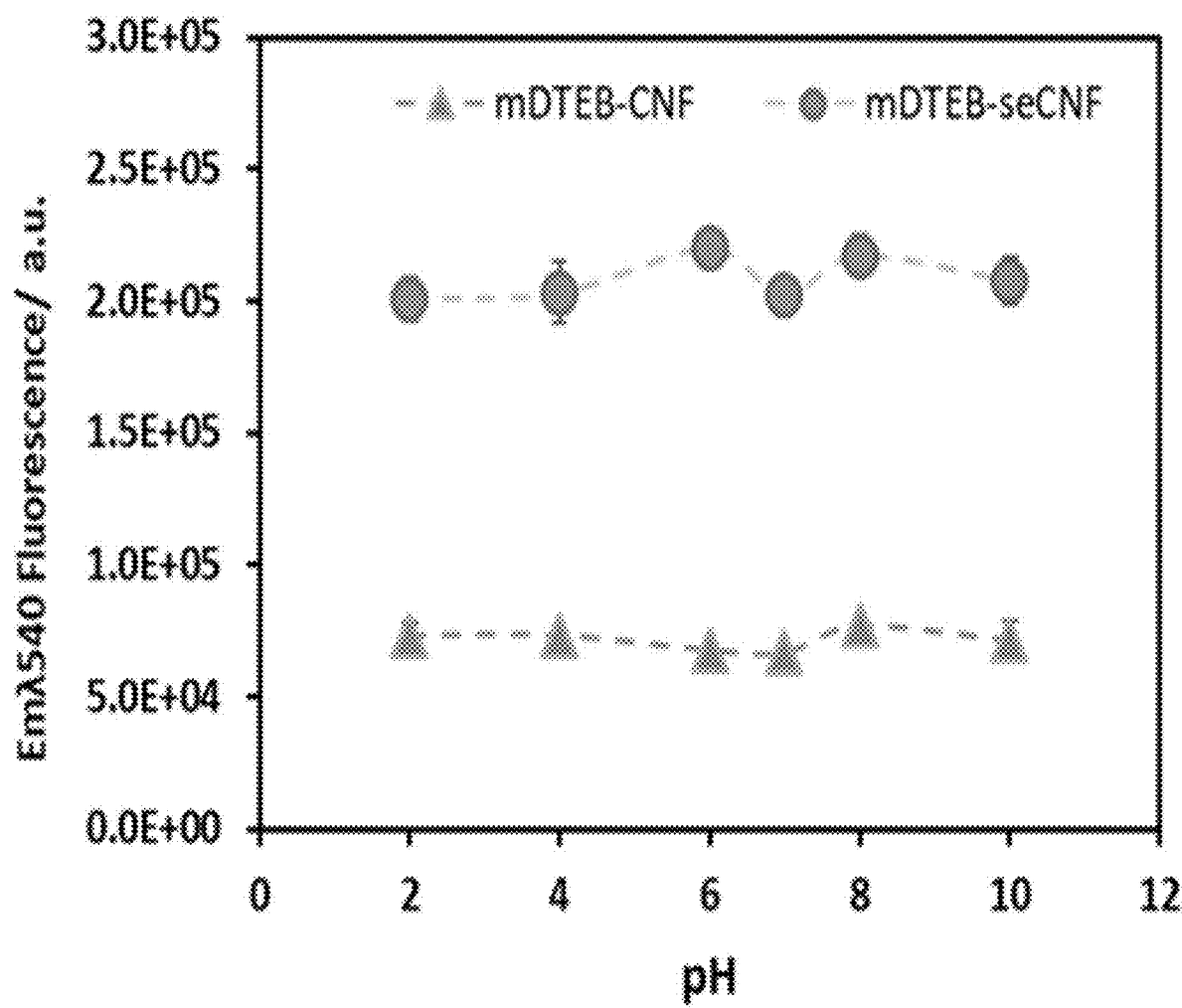
FIG. 9 shows pH-dependence fluorescence of labeled CNF (circle: mDTEB-seCNF, triangle: mDTEB-CNF)

Effect of pH and temperature on mDTEB-CNF and mDTEB-seCNF were examined fluorometrically. FIG. 9 shows stable fluorescence intensity over a wide pH range, from acidic to alkaline conditions, reflecting the stability of mDTEB labeled CNF at different pH. The stability is observed for both mDTEB-CNF and mDTEB-seCNF. Buffer types (chloride, citrate, phosphate, and glycine) did not affect the fluorescence of the labeled CNF, mDTEB-seCNF exhibited higher intensities compared to mDTEB-CNF at similar concentrations, indicating that surface impurities impact fluorescent labeling of CNF.

Figure 10:
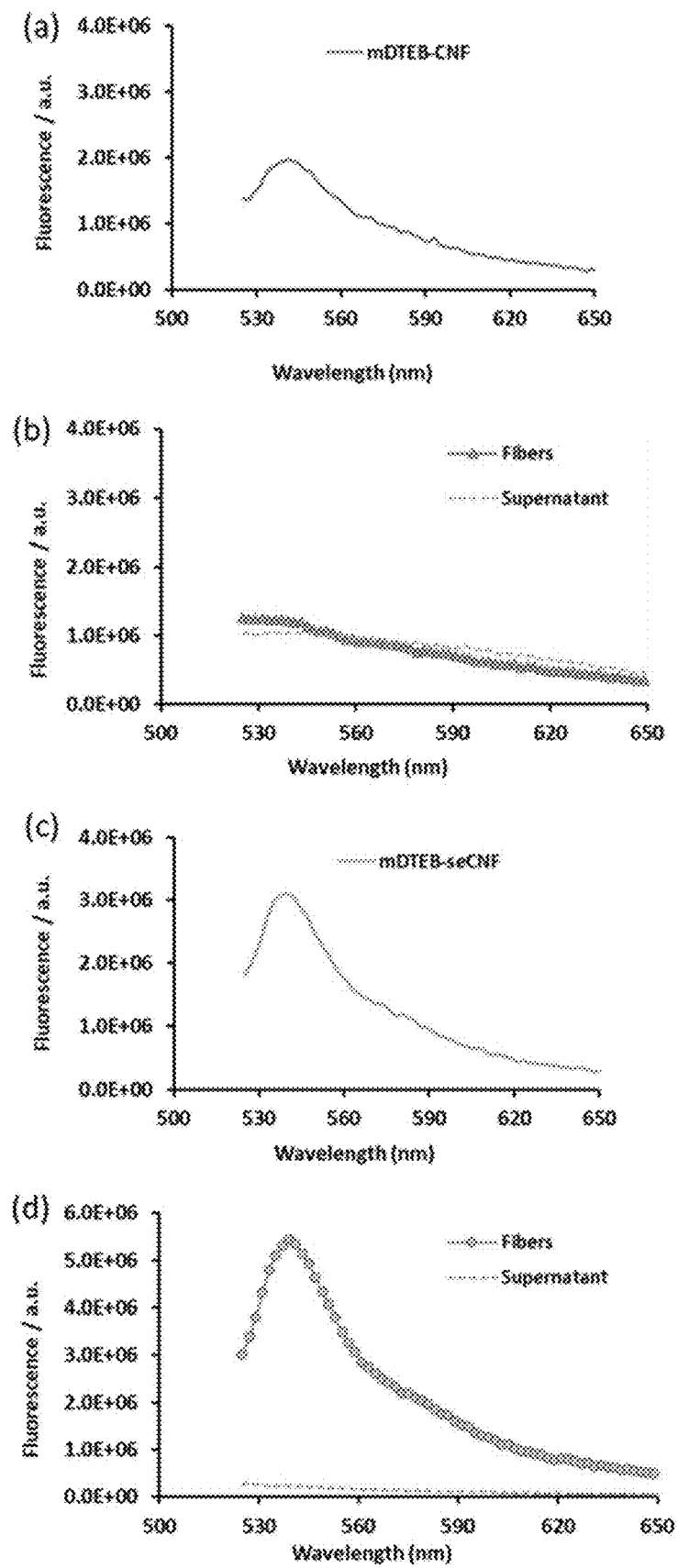
FIG. 10 shows temperature stability of mDTEB-CNF (a) fluorescence of mDTEB-CNF before autoclave, (b) fluorescence of mDTEB-CNF after autoclave, (c) fluorescence of mDTEB-seCNF before autoclave, and (d) fluorescence of mDTEB-seCNF after autoclave.

The temperature stability of the ether bond linkages under alkaline condition was assessed by autoclaving the labeled CNF at 105° C. for 15 min. FIG. 10 shows emission spectra of labeled CNF before and after autoclaving. mDTEB-CNF exhibited a significant reduction in fluorescence intensity after autoclaving (FIG. 10b), indicating that the fluorophore preferentially reacted with phenolic hydroxyl groups of lignin over the aliphatic hydroxyl groups of cellulose glucose units, which is highly correlated with the previous studies on lignin extraction from lignocellulosic material. On the other hand, mDTEB-seCNF exhibited no loss in fluorescence intensity after autoclaving (FIG. 10d), demonstrating the stability of this labeled CNF at high temperature. The observed fluorescence is likely dominated by covalent attachment of fluorescent probe with the hydroxyl groups of cellulose rather than surface impurities (e.g. lignin or other polyphenols).

Figure 11:
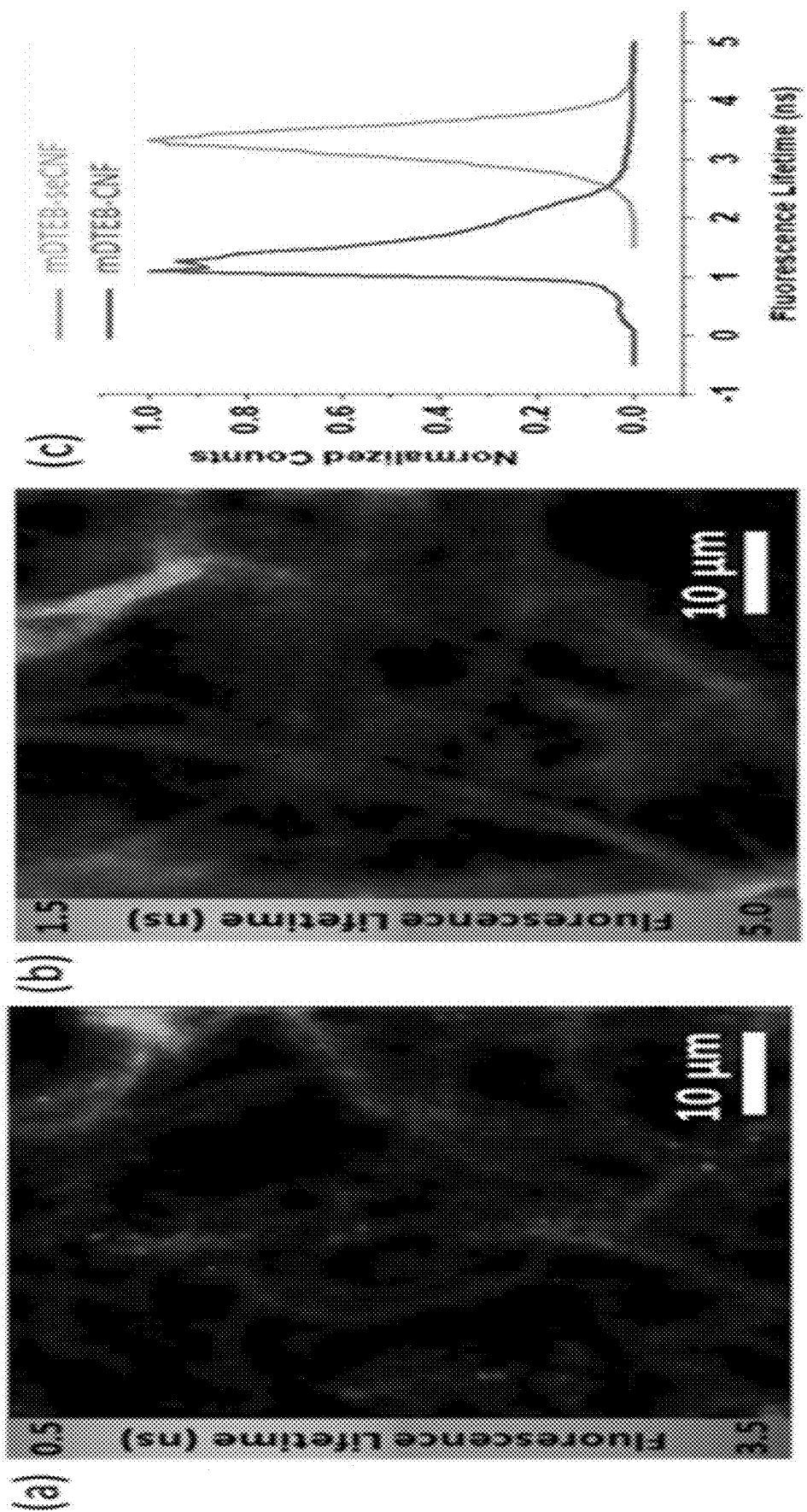
FIG. 11 shows fluorescence lifetime image of mDTEB labeled CNF (a) as received CNF w/mDTEB, (b) SE CNF with mDTEB, and (c) lifetime distributions of mDTEB-CNF.

Time correlated Single photon counting (TCSPC) Fluorescence lifetime imaging microscopy (FLIM) is used to check the quality of commercial CNF and probe the local environment of the mDTEB. The fluorescence lifetime of a fluorophore depends on its molecular environment but, within reasonable limits, not on its concentration. A fluorophore that is more mobile will have more opportunities for collisions or other non-radiative energy transfer and will have shorter lifetimes. Free fluorophore will have a shorter lifetime than physisorbed fluorophore, which will have a shorter lifetime than covalently bound fluorophore. In addition, it is expected that a fluorophore bound to lignin, which has random and chaotic linkage and branching leading to more degrees of freedom for a bound fluorophore and large number of aromatic groups capable of quenching fluorescence, will have a shorter lifetime than a fluorophore bound to cellulose. The unique fluorescence lifetime signatures of mDTEB in these various environments was used to distinguish fluorophore-CNF conjugates from fluorophore—lignin or lignin autofluorescence. The fluorescence lifetime distributions and ratiometric FILM images of mDTEB-CNF and mDTEB-seCNF are presented in FIG. 11. mDTEB-CNF exhibited two distinct lifetime distributions near 1 ns and 2 ns, whereas mDTEB-seCNF exhibited a single, narrow lifetime distribution centered at a longer lifetime of 3.5 ns. In addition, the total photon count for mDTEB-CNF was an order of magnitude lower than that for mDTEB-seCNF.

FLIM analysis also showed that lignin-like impurities, present on the surface of CNF, reduce the fluorescence intensity of mDTEB-CNF via quenching. As a result, the chemical composition and the methods of CNF production affect subsequent studies. Removal of these surface impurities is important for several reasons. First, autofluorescence from these impurities creates interference with or quenching of the dye. Second, even though cellulose constitutes the bulk of the fiber by mass, due to the stronger acidity of phenols over aliphatic alcohols, the dye will preferentially react with the lignin type impurities on the surface of the cellulose. Third, the impurities are not stable under extremely acidic or alkaline conditions and would likely be removed from the nanofiber during digestion. And fourth, the fluorescence lifetime of dye bound to these impurities is much shorter and broader than that of cellulose bound dye, leading to difficulties in differentiating bound dye from unreacted, free dye. These impurities can be mostly removed after labeling using the same methods to produce seCNF, however, the fluorescence intensity of the final product is greatly reduced.

Figure 12:
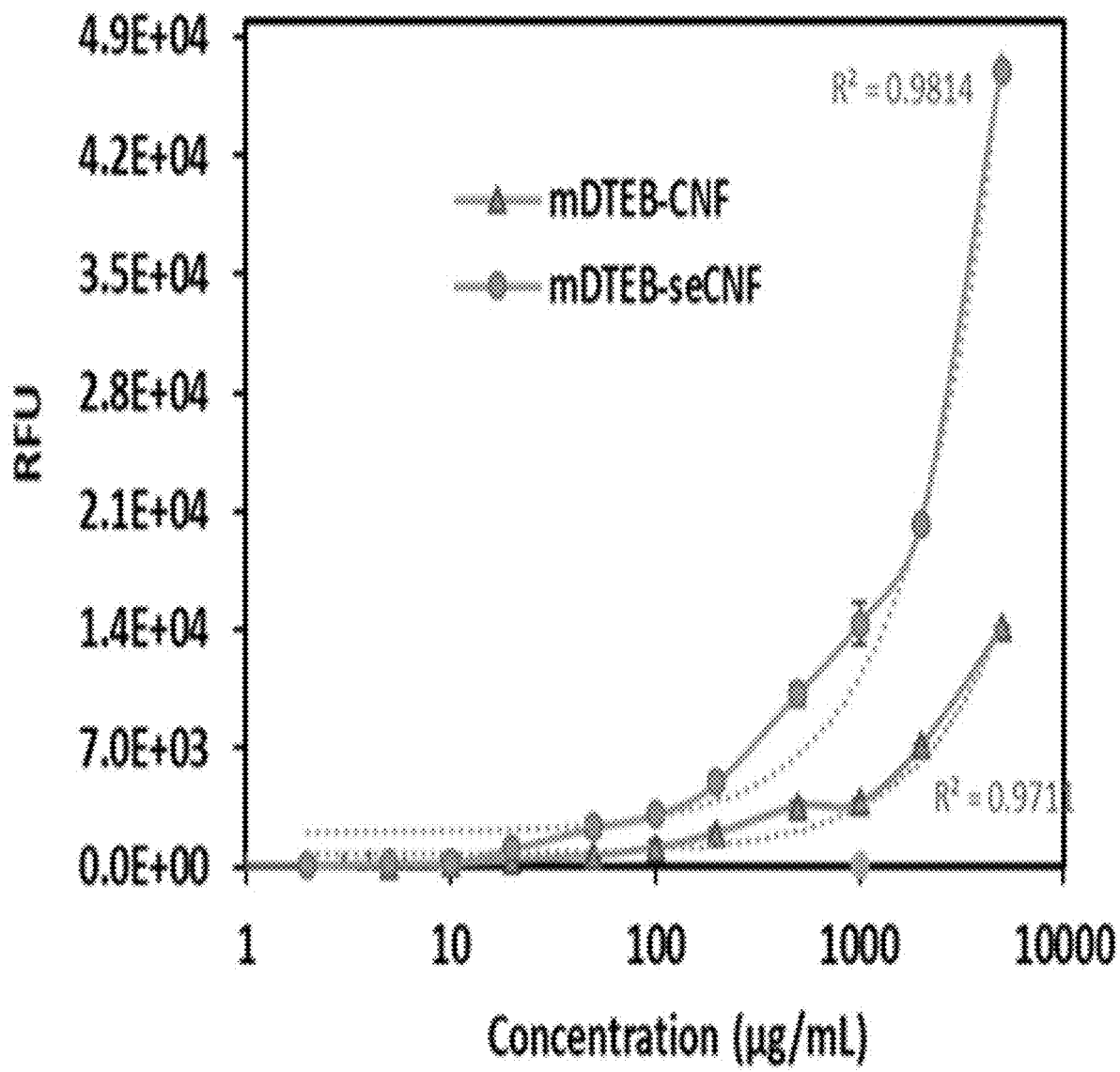
FIG. 12 shows concentration dependent fluorescence intensity of the labeled CNF (circle: mDTEB-seCNF, triangle: mDTEB-CNF)

Concentration-dependent fluorescence is important for both in vivo feeding and in vitro kinetics assays, as these assays require several fold dilutions of initial concentrations. In this context, the limit of detection for mDTEB-CNF and mDTEB-seCNF were determined in PBS buffer. mDTEB-seCNF can be detected under physiological conditions at concentration ranging from 2 µg/mL to 2000 µg/mL using a microplate reader (FIG. 12). Symmetrical emission peaks were observed at the lower concentrations. As the concentration increased, a scattering effect from the presence of fibers was observed, leading to asymmetrical emission peaks.

Figure 13:
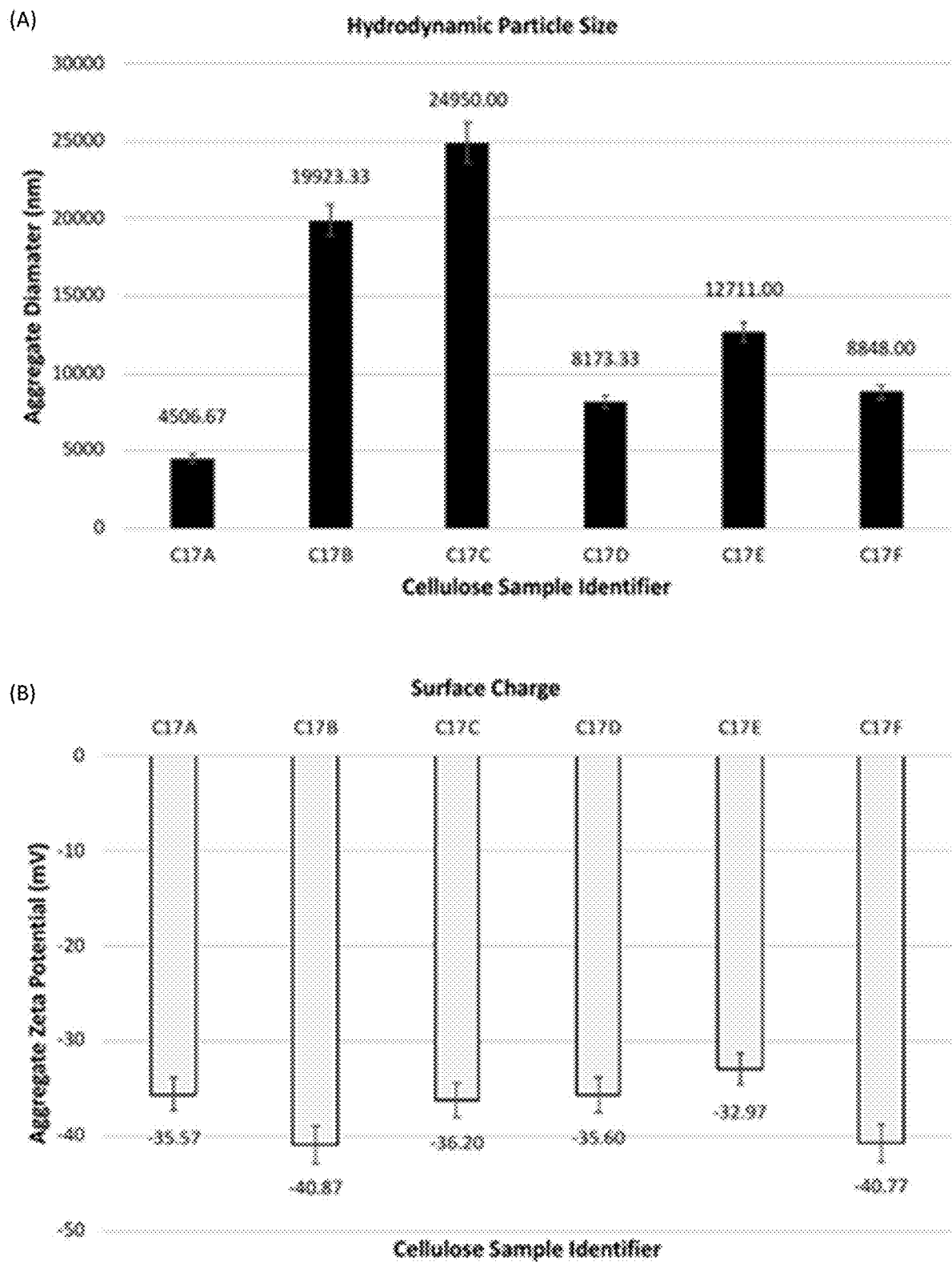
FIG. 13 shows hydrodynamic particle sizes (A) and zeta potential (B) of CNF materials, wherein materials are labelled as: C17A—CNF; C17B—rxn-CNF; C17C—mDTEB-CNF; C17D—seCNF; C17E—rxn-seCNF; C17F—mDTEB-seCNF.
Figure 14:
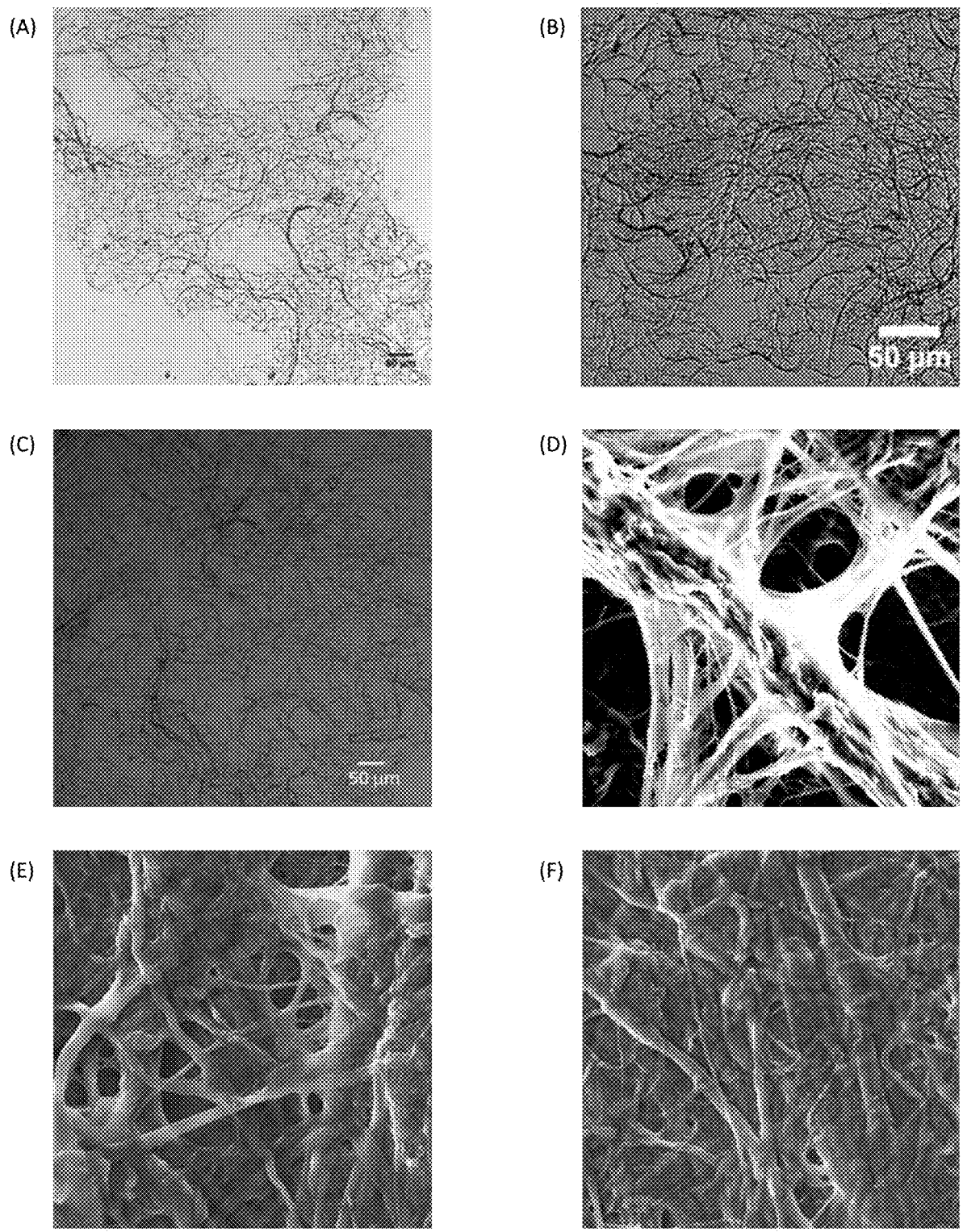
FIG. 14 shows wide field transmission micrographs of (a) CNF, (b) seCNF, and (c) mDTEB-CNF and SEM micrographs of (d) CNF, (e) seCNF, and (f) mDTEB-CNF.

Morphological and surface characteristics of the CNF were examined using dynamic light scattering (DLS), zeta potential (ZP), and inverse gas chromatography (iGC). It is well known that alkaline conditions cause separation and removal of lignin, increases in swelling and porosity, and changes in crystallinity in cellulosic materials. Not surprisingly, the basic reaction conditions during the labeling process, caused an increase in the apparent particle size of the CNF (FIG. 13a). The addition of the dye did not significantly affect the size. The surface extracted CNF did not show the same variation in particle size as was seen with the as received CNF. Although slightly larger than as received CNF, likely due alkali treatment, additional base treatment through the labeling process did not affect the seCNF size. This suggests that some of the size increase in as received CNF is due to de-binding of surface-adhered, lignin-like impurities. The surface charges of all samples (FIG. 13b) were largely unaffected by the reaction conditions. Wide field optical transmission images (FIG. 14a-FIG. 14c) and scanning electron microscopy images (FIG. 14d-FIG. 14f) provide additional evidence that the nano morphology is relatively unchanged after surface extraction and labeling.

Figure 15:
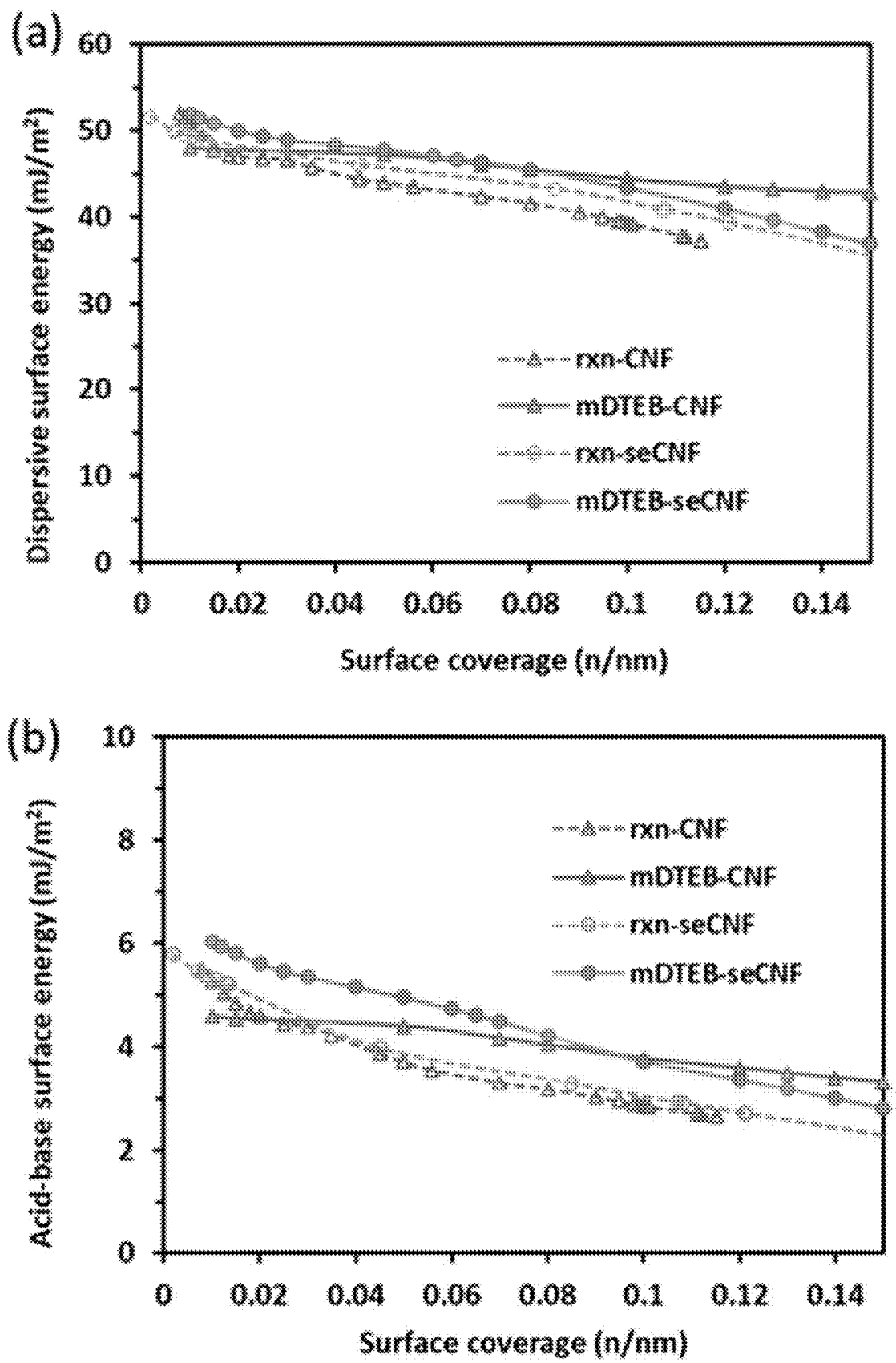
FIG. 15 shows (a) dispersive and (b) acid-base surface energy profiles for freeze-dried samples measured at 30° C., wherein fraction surface coverage is a number of moles (n) divided by a number of moles to cover a surface monolayer in nanometers (nm)

Inclusion of IGC in the analysis of the fluorescent CNF affords the opportunity to study the interactions between small probe molecules with different properties (such as octane and acetone) and the surface of solid samples. Linear alkane probes were used to determine the dispersive (van der Waals) interactions, while a series of polar probes was used to determine the acid-base character of the CNM. For these measurements, freeze-dried CNF samples were placed in a chromatographic column as the stationary phase, and solvent probe molecules were injected into the carrier gas stream. The retention time and shape of the chromatogram gives information on surface heterogeneity, surface area, acid-base properties, and surface energy. The colunm in iGC is filled with the solid sample under investigation (adsorbent) and the mobile phase consists of a probe molecule (adsorbate) with known properties to evaluate the surface of the adsorbent. Most solid samples have a range of surface energies due to defects, accessibility, and trace impurities. By performing experiments over a range of concentrations the heterogeneity of the surface energy can be elucidated. Dispersive and acid-base surface energy profiles for different CNF samples are shown in FIG. 15. The surface energy is noticeably higher at low surface coverage for each of the samples, which can be due to surface defects or impurities (FIG. 15). As received CNF samples had a dispersive surface energy value (<45 mJ/m$^2$) which is similar to wood base cellulose nanofibers. As received CNF have acid-base and dispersive energy profiles consistent for CNF produced from wood using mechanical methods. The alkaline treatment used to produce seCNF led to a slight increase in dispersive energy and no appreciable change in acid-base properties. Alkaline treatments are known to change the crystal structure of cellulose, which may have led to greater accessibility of the non-polar probes to the surface of seCNF. The covalent attachment of mDTEB led to slightly higher dispersive and acid-base energies, whether the CNF was surface extracted or not. The slight changes in surface energy are likely due to the introduction of bulky aromatic containing moieties. The pyranose ring of the unlabeled CNF, which accounts for the large dispersive energy of cellulose, becomes more accessible with the introduction of mDTEB, leading to a higher number or frequency of non-polar active sites and higher dispersion energy. Aromatic groups add basic interactions, which can account for the slight increase in acid-base properties of the labeled CNF relative to the unlabeled CNF. Although the changes in surface energy are small, these measurements show how small changes in surface groups can greatly affect surface energies and emphasizes the importance of avoiding over-labeling when modifying CNM.

After demonstrating that the new label was chemically stable, detectable at low concentrations of CNF, and suitable for digestive studies, the toxicity of the labeled CNF was evaluated in an in vitro small epithelial cellular model. In vivo toxicity and biodistribution of labeled CNF were evaluated in a zebrafish model.

Single-parameter in vitro tests can provide an indication of the relative concentrations at which a substance is toxic, as well as the mechanisms underlying the effects. To simulate an oral exposure of CNFs to the small intestinal epithelium, we applied digestas (from simulated 3-phase digestion) of the CNFs (at 0.75 and 1.5% by mass) in a fasting food model (phosphate buffer) to transwell and 96-well versions of a tri-culture small intestinal epithelium model. LDH release (cytotoxicity) and metabolic activity (viability, PrestoBlue) were measured after 24 h. The results of these experiments are summarized in FIG. 16*a*. No significant reduction in cell viability (reduction of the PrestoBlue reagent by mitochondrial reductases) was seen with either unlabeled CNF or mDTEB-seCNF at food concentrations up to 1.5% (by mass). It should be noted that the initial food concentrations are diluted by a factor of 48 during the digestion and preparation of samples, and the final concentrations applied to triculture cells were thus 0.015% and 0.03% by mass. These results indicate that neither labeled nor unlabeled CNF cause significant toxic effects on the small intestinal epithelium within 24 h.

Figure 16:
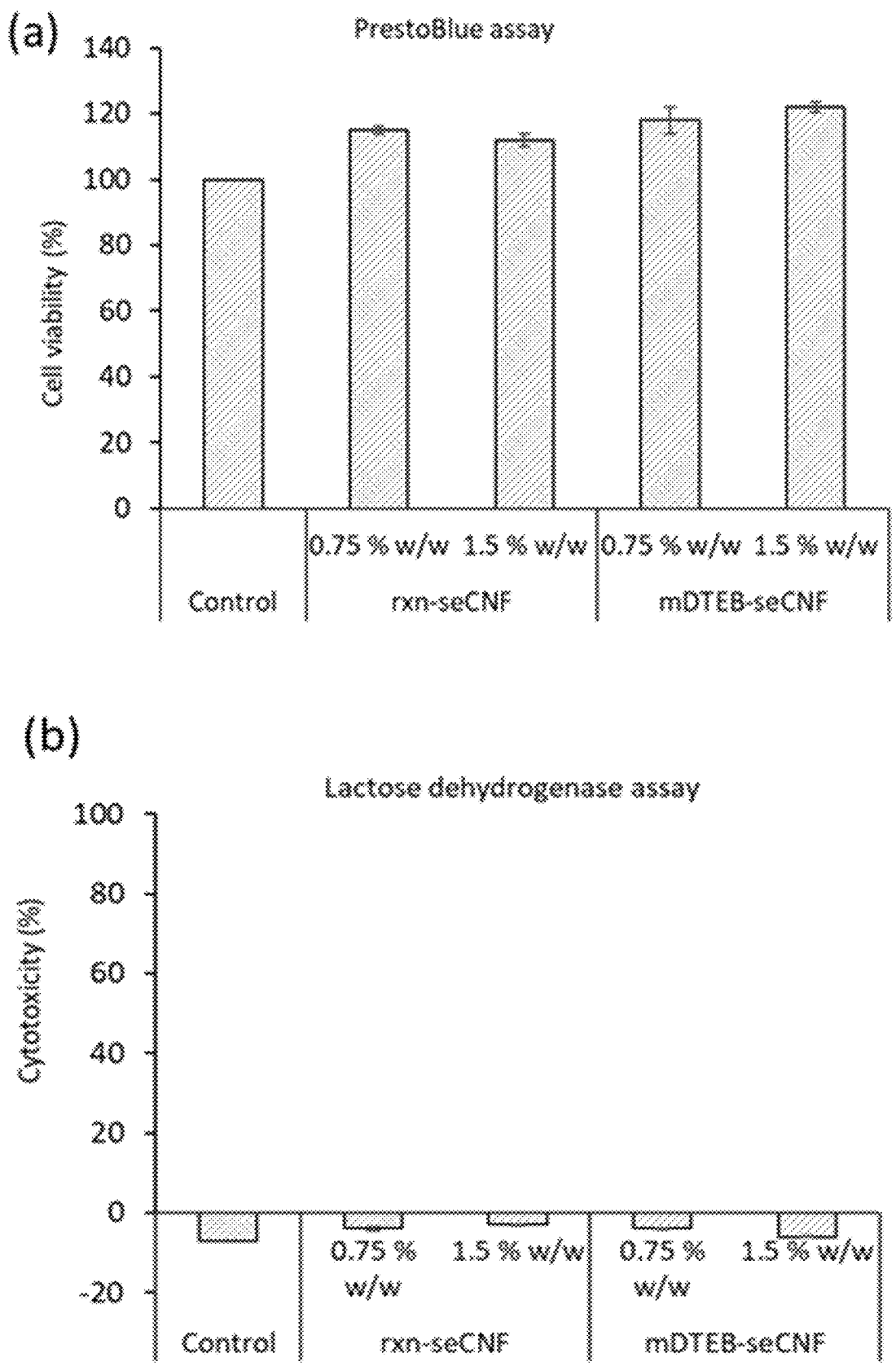
FIG. 16 shows cytotoxicity of CNF triculture epithelium exposed to CNF digesta. (a) PrestoBlue assay (n=4) (b) LDH assay (n=4)

The absence of cytotoxic effects was confirmed by measurement of LDH release, an indicator of plasma membrane damage, in the triculture epithelial cells exposed to CNF-containing digestas (FIG. 16*b*). LDH release from cells treated for 24 h with CNF-containing digestas was significantly lower than in cells treated with control digestas (without CNF). Together, the PrestoBlue and LDH results suggest that labeled and unlabeled CNF materials are non-toxic in an in vitro small intestinal epithelial model. These findings agree with other in-vitro and in-vivo studies published by the authors on various CNF and CNC materials.

Figure 17:
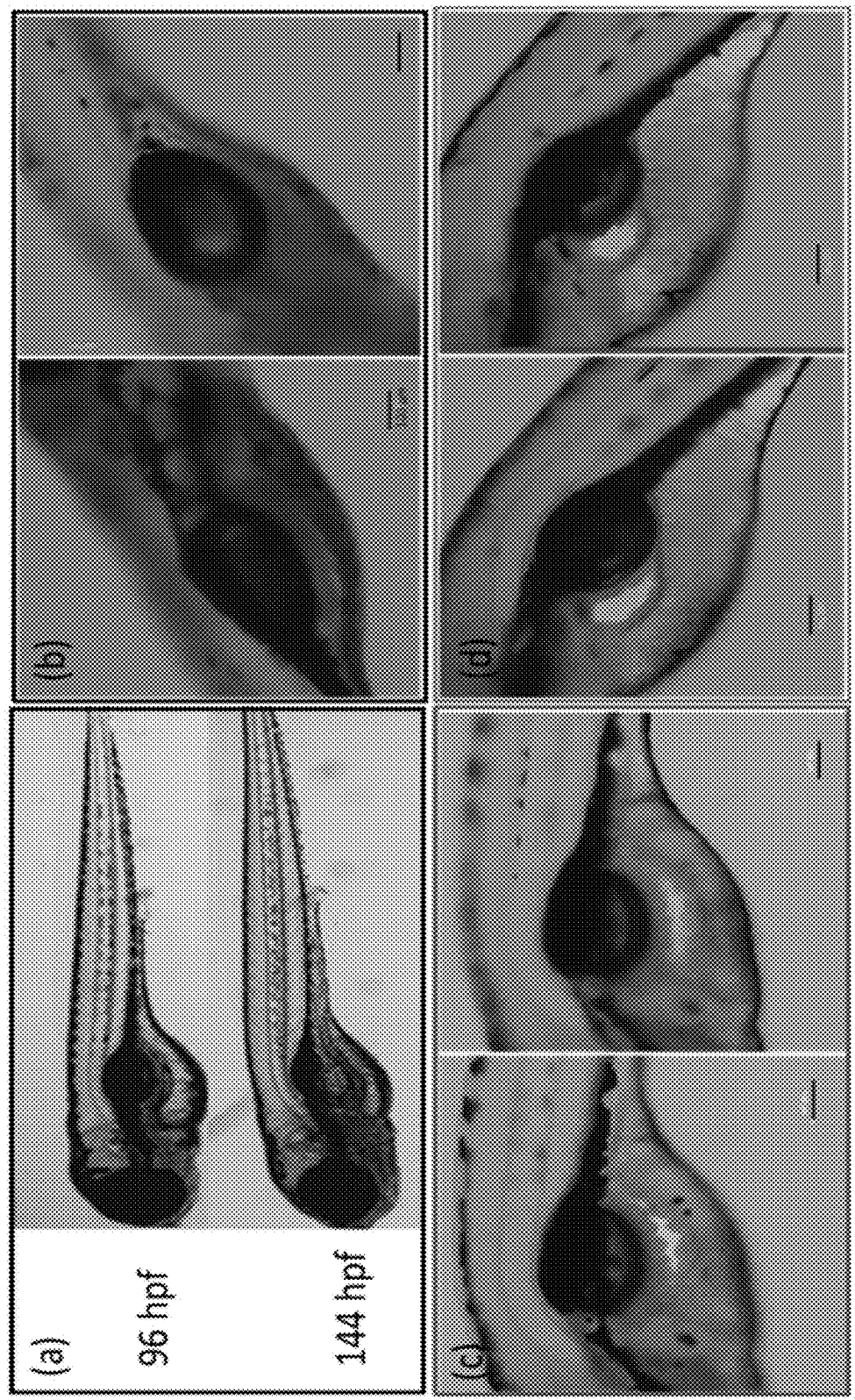
FIG. 17 shows confocal images of mDTEB labeled CNF uptake in zebrafish yolks sac after 96 h and 144 h post fertilization for (a) 4-5 days old zebrafish, (b) autofluorescence in yolk sac, (c) mDTEB-CNF, and (d) mDTEB-seCNF.

This Example has shown that the fluorophore-labeled CNF exhibits the desired fluorescence, allowing precise imaging by confocal laser scanning microscopy. As such, it may serve as a potential biomarker that allows for the fluorescence-based optical detection of CNF uptake and distribution in living organisms. Zebrafish embryos at 96 hours post-fertilization (hpf) were exposed to mDTEB-labeled CNF samples, and fluorescence imaging was performed at 144 hpf which allowed for oral exposure as a result of the mouth gaping behavior. Using this technique, we visualized uptake of the fluorescent CNF within the GI tract and follow its distribution to the anus of the fish (FIG. 17). Although there was some naturally occurring autofluorescence within discrete small sections of the yolk sack of control fish (FIG. 17B), the fluorescence images revealed the presence of the luminescent mDTEB-CNF and mDTEB-seCNF throughout the yolk sack at a much higher intensity (FIG. 17C and FIG. 17D, respectively). There was no embryo mortality as a result of exposure to either of the nanofibers, supporting the low toxicity of mDTEB-CNF towards developing zebrafish following both dermal and oral exposure. In addition, tests with similar concentrations and increasing up 0.36% by mass of unlabeled CNF caused no significant toxicity, and no change in toxicity can be noted following conjugation of the materials with the test fluorophores. These results are further supported by previous studies of lignin nanoparticles showing they are of very low toxicity to zebrafish embryos. These results are supporting data that highlight the nontoxicity of the mDTEB-CNF and, as a new kind of nanomaterial based on wood, important for demonstrating their biocompatibility for their future use in food and pharmaceutical applications.

It should be appreciated that mDTEB is a two-photon fluorescent probe that is based on a BODIPY skeleton and attached to CNF in aqueous solution for the quantitative tracking CNF in biological media, i.e. gastrointestinal tract system. The labeled CNF was assessed for its suitability in digestive studies, where environmentally harsh conditions exist. mDTEB-CNF was stable over a wide pH range, from pH 2 to pH 10, and was thermally stable under autoclave conditions. The labeled CNF was detectable to 2 μg/mL. Fluorescence lifetime imaging microscopy showed that lignin like surface impurities had an impact on the labeling chemistry, indicated by the observation that mDTEB-seCNF had higher fluorescence lifetimes compared to as mDTEB-CNF. Removing these impurities prior to labeling was important for maintaining the low detection limit needed for ingestion exposure studies. Surface characterization measurements showed that the label did not significantly alter the hydrodynamic radius of the nanofibers, the surface charges, or the surface energy of the CNF, indicating that the mDTEB-seCNF materials were physicochemically and morphologically representative of commercially produced CNF. The toxicity of CNF was found to be low using the mDTEB-CNF in simulated digestion and in vitro small intestinal epithelial model experiments, and in in vivo zebrafish ingestion and biodistribution analyses.

Example 2. MDTEB, a Fluorescent Label for Carbohydrate Nanomaterial In Vivo Studies Typical studies of gastral toxicity of nanoparticles are conducted using radio labeling. This tends to be quite expensive and difficult owing to the required protocols for working with these materials and the expense of the chemical reagents. An alternative is fluorescence labeling. Fluorescence is just as sensitive as scintillation given that scintillation is itself a fluorescence measurement and subject to the same limitations. However, most fluorophores are sensitive to changes in pH and hydrolysis reactions present in most mammalian digestive tracts. This Examples describes synthesis of a new pH insensitive and hydrolytically stable fluorophore, 10-(4-(3,5-dichlorophenoxy)phenyl)-2,8-diethyl-5,5-difluoro-1,3,7,9-tetramethyl-5H-4l4,5l4-dipyrrolo[1,2-c:2',1'-f][1,3,2]diazaborinine (mDTEB). This fluorophore is based on the high quantum yield Boron-dipyrromethene (BODIPY) fluorescent center and is equipped with a reactive handle for convenient attachment to polysaccharides. We validate its effectiveness by labelling cellulose nano fibers (CNF), where the importance of removing reactive lignin to prevent quenching enables preparation of homogeneously labelled bright m DTEB-CNF for toxicity studies.

Carbohydrate nanomaterials (CNM) are a class of compounds in a growing number of applications. In particular, they have been identified in many applications that involve potential CNM ingestion, such as in the protection and delivery of bioactive compounds and nutrients, bioconjugation of metal nanoparticles for improved biological interfaces, biosensor design, wound dressings, tissue engineering, food coatings and packaging, and food additives. The commercialization of these materials often requires knowledge of the absorption, distribution, metabolism, and excretion (ADME) of the material in animals.

Radiolabels are relatively easy to detect in samples of tissues and body fluids. The radiolabel should be uniformly distributed in the molecule and should not be biologically labile. However, radiolabeling carbohydrate nanoparticles is particularly challenging. Cellulose and starch have been labeled by growing plants in radioactive nutrients, but that requires subsequent processing of the radioactive material into the nano form. Obtaining the licensing, dedicating the necessary processing equipment, tracking all radioactivity during processing steps, and handling the large amount of radioactive waste are daunting challenges. Labeling the nanomaterials with a small radioactive tag is also challenging, primarily because most carbohydrates must be processed in water to prevent irreversible aggregation of the particles, which destroys the desired nano-morphology. As an alternative, fluorescent dyes have often been used to track carbohydrate nanoparticles in vivo, since they offer the advantages of covalent attachment and detection limits close to that of radiolabels.

Fluorescently labeled carbohydrate nanoparticles can be used such as use of Rhodamine B derivatives for biological applications because it is relatively photostable, has a high quantum yield, readily penetrates cell membranes, and the excitation and emission bands are red-shifted compared to most auto fluorescing molecules found in nature. However, the quantum yield and attachment chemistries are only stable over a narrow pH range, leading to challenges in digestive studies where the pH ranges from 1.5 in the stomach to about 9 in the colon. Therefore, the only viable (stable) attachment chemistries for digestive studies are amide bonds and ether bonds. The amide linkage requires either an amine or a carboxylic acid functionality on the carbohydrate. Although these are present on some polysaccharides, such as chitin, chitosan, and alginic acid, they are absent on polysaccharides such as cellulose and starch. Amine functionalization of cellulose requires multiple reaction and purification steps, and often significantly changes the surface chemistry of the carbohydrate. The ether bond can be formed using fluorescent dyes with dichlorotriazine functionality. These have been used extensively to functionalize nanocellulose and starch. However, there are only two that are commercially available: 5-(4,6-Dichlorotriazinyl) aminofluorescein (DTAF) and Texas Red C2-dichlorotriazine (TR). DTAF, which is based on a fluorescein structure is not photostable and the quantum yield is extremely dependent on the pH of the medium. TR is much more photo and pH stable, but it has a very low quantum yield. So, there is a need for new hydroxyl-reactive fluorescent dyes to enable reliable ADME and pharmacokinetic studies of polysaccharides.

Boron-dipyrromethene (BODIPY) dyes are a very popular choice for biological applications. Most BODIPY dyes have high quantum yields, are photostable, have environment-independent quantum yields, are relatively chemically stable, are of low toxicity, and can be structurally modified to generate a desired excitation wavelength. Due to their high stability and great chemical versatility, BODIPY are an ideal candidate for the synthesis of a carbohydrate nanoparticle specific label.

Figure 18:
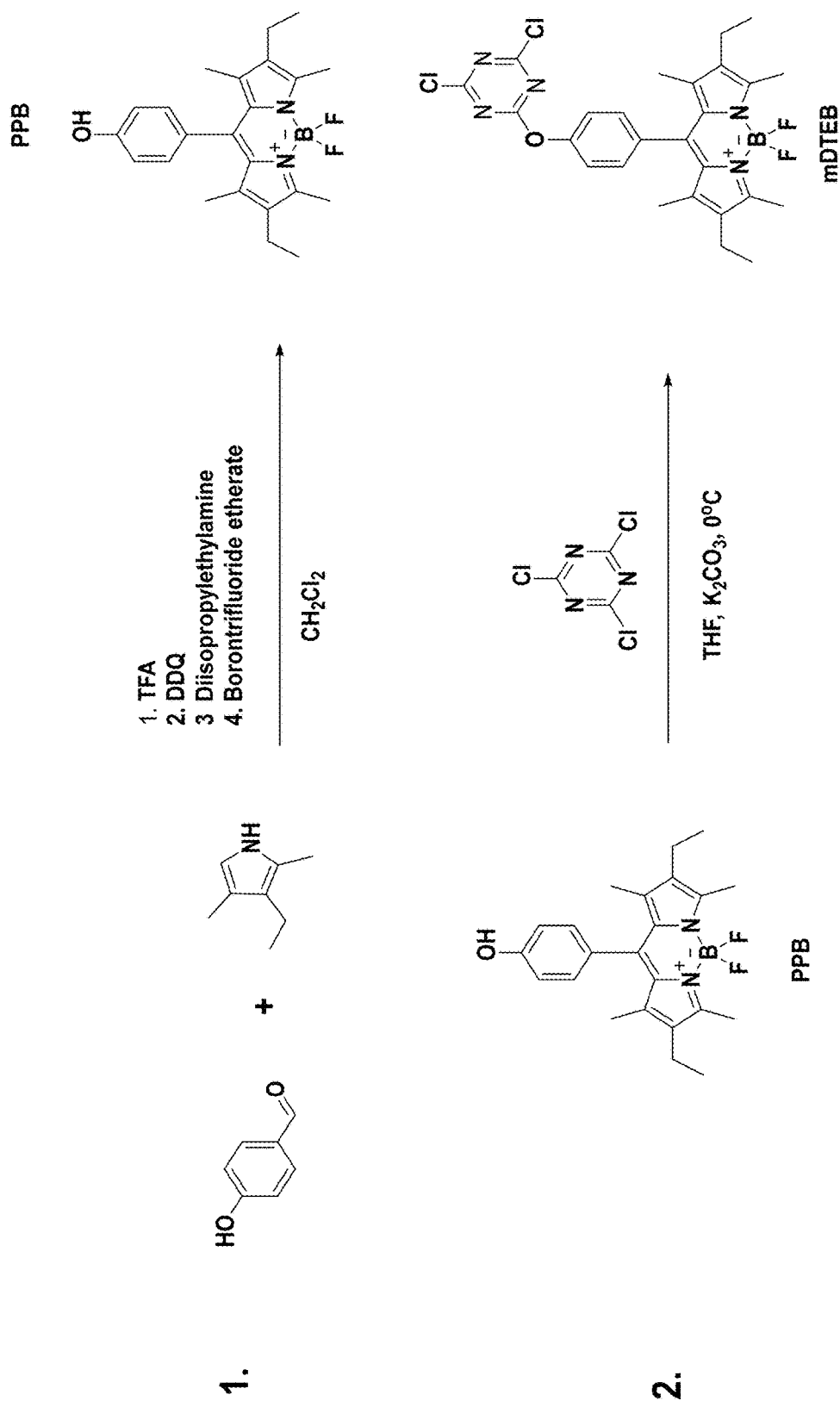
FIG. 18 shows synthesis of mDTEB: 1. Synthesis of PPB using a one pot, four step synthesis. 2. Reaction of PPB with trichlorotriazine to form mDTEB.

This Example describes synthesis of a BODIPY dye referred to as mDTEB that chemically attaches to polysaccharides and overcomes the issues discussed above. The BODIPY core was modified with ethyl groups (see FIG. 18) to present a chemically stable periphery to aqueous media and to inhibit attacks on the redox sites and the electrophilic sites of the indacene core. The purified product was characterized using solution NMR and fluorescence measurements. The dye was used to label cellulose nanofibrils (CNF) which were characterized using fluorescence lifetime imaging microscopy (FLIM).

Methylene chloride was dried using a solvent purification system. Native as—received cellulose nanofibrils (AR-CNF) were used or first autoclaved at 100° C. in base to remove lignin (AC-CNF).

With regard to fluorescence lifetime imaging microscopy (FLIM), FLIM was conducted on a custom build microscope at NIST. The excitation was performed using a Ti-Sapphire laser with a pulse width of 140 fs passed through SHG frequency doubling optics that emitted at 514 nm with an average pulse power of 0.5 µW. The sample excitation used an air objective with a numerical aperture of 0.75. The images were collected by raster scanning the laser focus using an X-Y piezo stage. The resulting fluorescence was collected through the same objective and sent to single photon counting modules for lifetime measurements through a notch filter to remove excitation light. The images were then analyzed using SPCImage NG software package and subject to threshold at 50 counts to remove background noise. The decay curves were fit using an algorithmically estimated IRF for each pixel. Phasors were generated using the time domain methodology with equation 1 and equation 2, where g(ω) and s(ω) are x and y coordinates of a cartesian plot. The phasors were then exported and plotted based on the functions:

$$S_i(\omega) = \frac{\int_0^\infty I(t)\sin(n\omega t)dt}{\int_0^\infty I(t)dt} \text{ and}$$

$$G_i(\omega) = \frac{\int_0^\infty I(t)\cos(n\omega t)dt}{\int_0^\infty I(t)dt},$$

wherein ω is the angular repetition frequency of the excitation source; n is the harmonic frequency, I(t) the decay at each time in each pixel.

With regard to dye synthesis, 4-(2,8-diethyl-5,5-difluoro-1,3,7,9-tetramethyl-5H-4l4,5l4-dipyrrolo[1,2-c:2',1'-f][1,3,2]diazaborinin-10-yl)phenol (PPB) was synthesized in which 4-hydroxy benzaldehyde (219.0 mg, 1.79 mmol) and freshly distilled 3-ethyl-2,4-dimethylpyrrole (379.8 mg, 3.42 mmol) were dissolved in 5 mL of methylene chloride under nitrogen atmosphere. One drop of trifluoroacetic acid was added and the reaction was stirred for 1.5 h after TLC confirmation of aldehyde consumption. Then, 2,3-dichloro-5,6-dicyano-1,4-benzoquinone (DDQ, 488.0 mg, 2.5 mmol) dissolved in 5 mL methylene chloride was added to the solution through a purged syringe. The reaction was then stirred for 1 h. The reaction flask was then lowered into an ice bath and brought to 0° C. Diisopropylethylamine (2.55 g, 17.9 mmol) was added using a purged syringe dropwise. The reaction was then stirred for 0.5 h. While still in the ice bath, boron trifluoride etherate (2.32 g, 17.9 mmol) was added using a syringe, dropwise due to the presence of an exotherm. The reaction was then stirred for 10 h. The reaction mixture was dispersed in 100 mL methylene chloride and washed three times with 100 mL saturated aqueous sodium bicarbonate, followed by three 100 mL washes with deionized water. The organic layer was then dried over anhydrous sodium sulfate. PPB was isolated via column chromatography as a vibrant red solid with silica gel as the stationary phase and chloroform/ethyl acetate/hexanes (v:v, 1:1:3) solvent as mobile phase in a 25% yield. $^1$HNMR: (CDCl$_3$): δ (ppm) 7.1 (m, 2H, aromatic), 6.9 (m, 2H, aromatic), 2.5 (3H, S, CH$_3$), 2.3 (4H, q, CH$_2$), 2.2 (3H, S, CH$_3$), 1.3 (9H, S, CH$_3$), 1.0 (3H, t, CH$_3$). Mass Spec, +M 396.4.

With regard to synthesis of 10-(4-(3,5-dichlorophenoxy)phenyl)-2,8-diethyl-5,5-difluoro-1,3,7,9-tetramethyl-5H-414,514-dipyrrolo[1,2-c:2',1'-f][1,3,2]diazaborinine (mDTEB), PPB (10 mg, 18.3 μmol) and potassium carbonate (10 mg, 72.0 μmol) were placed in dry THF (2 mL) in a two necked round bottom flask under an argon atmosphere. The flask was lowered into an ice bath and allowed to stir for 30 minutes. Cyuranic chloride dissolved in dry THF (1 mL) was added using a purged syringe dropwise to the reaction mixture. The reaction was stirred for 10 h. The mDTEB was isolated by column chromatography using acidic alumina as the stationary phase and hexanes/ethylacetate (v:v 1:1) as the mobile phase. The dye structure was confirmed using $^1$H NMR and used immediately to functionalize the cellulose. $^1$HNMR: (CDCl$_3$): δ (ppm) 7.2 (m, 2H, aromatic), 6.6 (m, 2H, aromatic), 2.5 (3H, S, CH$_3$), 2.3 (4H, q, CH$_2$), 2.2 (3H, S, CH$_3$), 1.3 (9H, S, CH$_3$), 1.0 (3H, t, CH$_3$).

With regard to cellulose labeling, cellulose nanofibrils (CNF with 20 mass % water) (4.5 g of dry wt.) were added to Na$_2$CO$_3$ solution (150 mL 50 mM) and stirred for 30 min. An additional 100 mL of water was added to facilitate stirring. mDTEB (2 mg) was dissolved in 500 μL of acetone, then added to the alkaline CNFs suspension and stirred for 72 h in the dark at room temperature. When the reaction was completed, the modified CNFs were isolated by centrifugation (500 rad/s (5000 rpm) for 20 min). After centrifugation, the excess of mDTEB was removed by washing labeled CNFs with 3×100 mL of an ethyl acetate—water mixture. Purification was carried out using a mixer at 157 rads/s 1500 rpm for 10 min followed by centrifugation at 4000 rpm for 10 min. The purification step was repeated until no fluorescent signal was detected in the washing liquor. The CNFs were resuspended in water and repeatedly centrifuged until the ethyl acetate solvent was completely removed. The labeled CNF was analyzed using an NIST built, time correlated, single photon counting FLIM instrument utilizing a femtosecond Ti-sapphire laser. Samples were excited using 514 nm laser light. An air objective with a numerical aperture of 0.9 was used for imaging. The FLIM images were acquired by building up fluorescence decay curves at each pixel. The decay curve was subsequently fit using a single or multi exponential to determine the lifetime at that pixel. The images presented are 30 μm×30 μm (256 pixels× 256 pixels) with an integration time of 40 ms/pixel.

Figure 19:
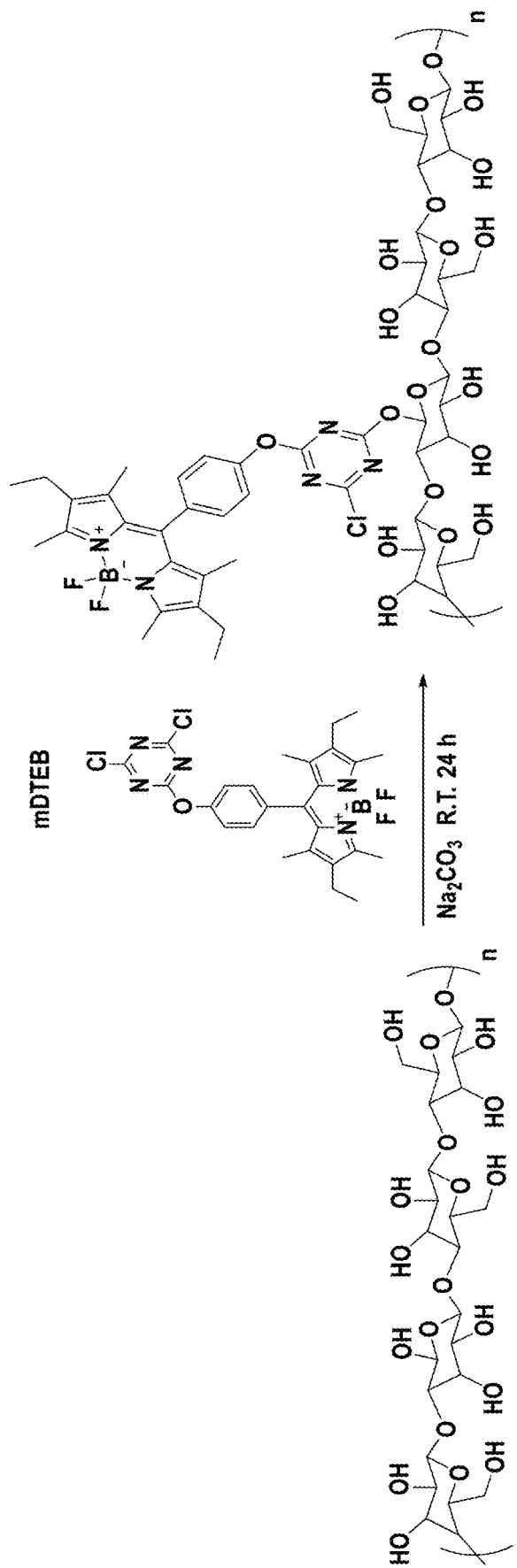
FIG. 19 shows reactivity of mDTEB by solvation in acetone with addition to a stirred dispersion of CNF in aqueous sodium carbonate.
Figure 20:
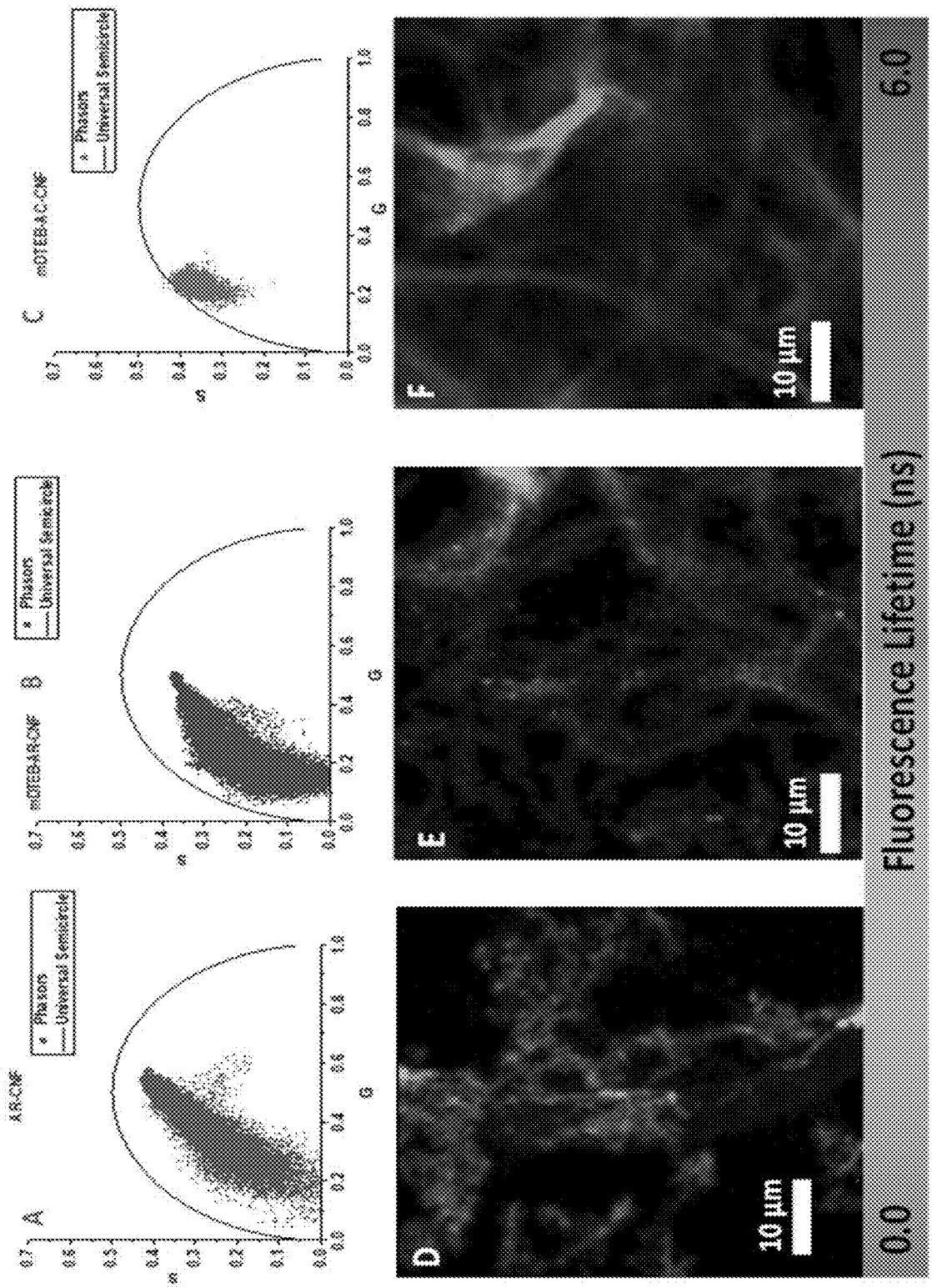
FIG. 20 shows phasor plots for cellulose nanofibers: (A) mDTEB functionalized as received CNF; (B) autoclaved CNF; and labeled with mDTEB (C); and image maps for: false colored fluorescence lifetime maps for CNF (D), mDTEB functionalized CNF (E), and autoclaved CNF functionalized with mDTEB (F), wherein a scale for false color is shown below image maps for image threshold of 50 counts for background noise removal.
Figure 21:
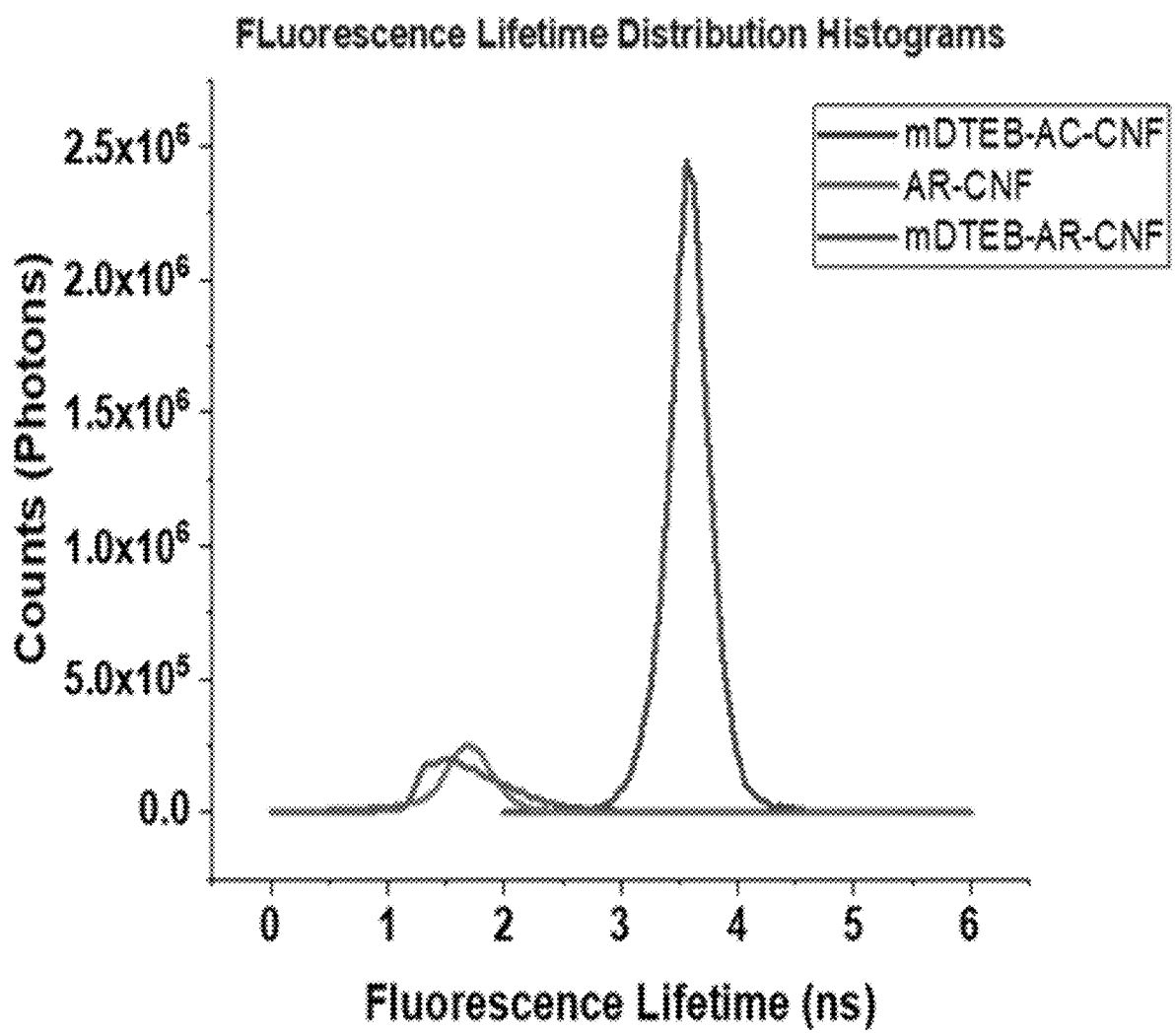
FIG. 21 shows average fluorescence lifetime distributions for AR-CNF, mDTEB-AR-CNF, and mDTEB-AC-CNF. AR-CNF and nDTEB-AR-CNF involved double exponential fit for two-component lifetimes. Also, nDTEB-AC-CNF was fit with a single exponential and showed stronger fluorescence for a homogeneous dye environment and covalent attachment.

Using the nDTEB discussed above and the method shown in FIG. 19, labelled CNF were initially prepared using as received CNF, designated mDTEB-AR-CNF. Since FLIM is often used to confirm dye-functionalization of biopolymers it was employed here. Comparison of the data before and after the mDTEB reaction shows very little change in both the FLIM images (FIG. 20D versus FIG. 20E) or the phasor plots (FIG. 20A versus FIG. 20B). This is further confirmed by examination of the lifetime distributions shown in FIG. 21, where the distribution peak for the AR-CNF, from the autofluorescence of lignin on the AR-CNF, appears similar to the lifetime distribution peak after treatment with mDTEB (mDTEB-AR-CNF). Lignin contained on the AR-CN surface was interfering with the cellulose alcohol reaction with mDTEB, and that the lignin was quenching any mDTEB that had reacted, either with the cellulose or the lignin itself. Chemical modifications of wood have shown a very high reactivity of the lignin present in the wood. This is due to the multiple diverse structures of lignin which are more reactive than the aliphatic alcohols of cellulose. Furthermore, it has been shown that lignin undergoes a self-quenching mechanism.

Indeed, autoclave cleaning (105° C., 15 min, 0.1 M aq NaOH) of the CNF, which removes the lignin (designated AC-CNF) and the autofluorescence, followed by reaction with mDTEB did produce the expected enhancement in fluorescence. This is clear from comparison of the FLIM images in FIG. 20F to that in FIG. 20D or FIG. 20E. The successful attachment of mDTEB to the AC-CNF is further supported by the lifetime distributions shown in FIG. 21, where the peak intensity for mDTEB-AC-CNF is an order of magnitude greater and the average lifetime is more than doubled (1.5 ns versus 3.5 ns). In addition, the data for mDTEB-AC-CNF fluorescence lifetime decay curve only requires a single exponential fit, and the phasor plot data for mDTEB-AC-CNF appears at the universal semicircle at about 3.5 ns (note the tight clustering of the red pixels, FIG. 20C). The single exponential fit and the clustering of the pixels on the universal semicircle is characteristic of fluorophores in very similar environments. In addition, the FLIM image in FIG. 20D of the labeled clean CNF shows uniform labeling (green color), thus confirming covalent attachment.

An additional concern for mDTEB labelled AR-CNF is that is quite possible that a large portion of the dye could be removed during ADME or pharmokinetic studies, i.e., in the biochemical environment mDTEB attached to lignin could be seperated from the CNF. This would produce erroneous results. To confirm this possibility we autoclaved the mDTEB-AR-CNF at pH 13, to produce AC-mDTEB-AR-CNF and found that the sample was no longer fluorescent. However, the same autoclaving of the mDTEB-AC-CNF produced a sample (AC-mDTEB-AC-CNF) with persistent fluorescent. This implies that the mDTEB reacted with surface lignin, rather than the cellulose, and was removed with the lignin by the autoclaving process. It also further reinforces the need to label cellulose after autoclaving with base treatment to enhance the targeting of cellulose alcohols. Clearly, the impact of the lignin is significant regarding labeling efforts targeted at cellulose.

Figure 22:
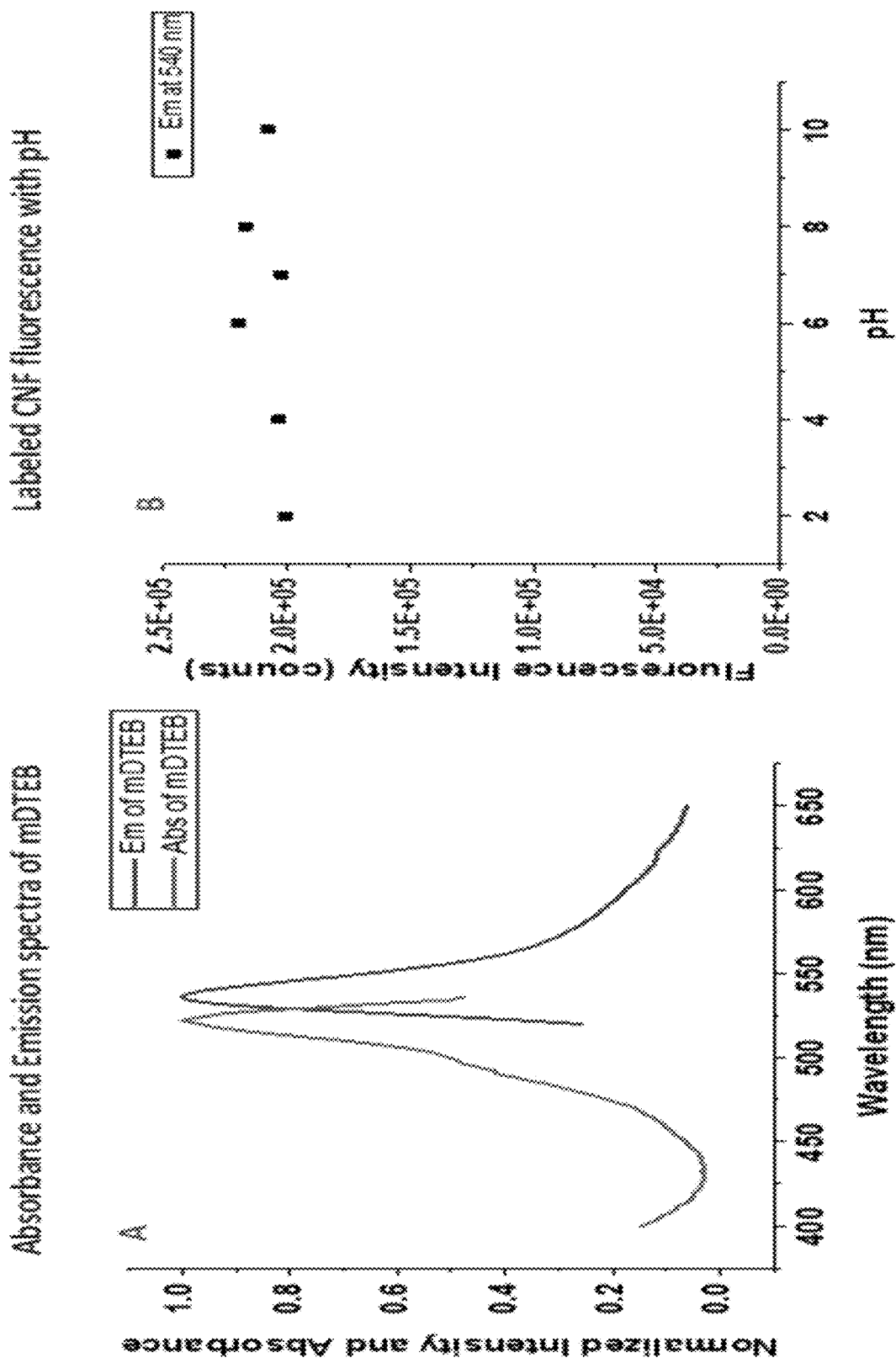
FIG. 22 shows (A) an absorbance spectrum and emission spectrum of mDTEB labeled CNF in water; and (B) a graph of fluorescence intensity as a function of pH for mDTEB labeled CNF.

There is a need for pH stable and pH insensitive dyes that can be covalently bound to polysaccharides for ADME and pharmacokinetic studies. This agnostic nature needs also extend to the chemistry binding the dye to the CNF. It is also desirable that these dyes have absorbances and emissions outside that found in biological systems. As can be seen in FIG. 22A, the absorbance peak of mDTEB is at 514 nm with the emission peak at 540 nm. The narrow stoke shift (36 nm) is typical of the Bodipy family of dyes. The alkylation of the core indacene ring structure at the 1,2,3,5,6 and 7 positions, red shifts the absorbance and emission of the dye and sterically protects the electrophilic centers at these positions. This may also aid in the inhibition of oxidation. To evaluate the pH effect on fluorescence of mDTEB-AC-CNF the emission intensity of mDTEB labeled CNF was monitored as a function of pH (FIG. 22B). The observed intensity did not vary significantly with changes in pH. The dyed CNF remained stable at pH values ranging from 2 up to a pH of 10. This is well within the range found in biological settings as well as in the gastral tracts of most mammals.

Here, mDTEB, a dye, was synthesized with a Bodipy core that was reactive with CNF, formed an ether type bond with alcohols, and was stable to a wide range of pH values. In addition, the green emission at 540 nm is insensitive to pH. The presence of lignin can confound the labeling of cellulose as well as diminish the fluorescence signal from the dye. Removal of lignin is necessary for clean labeling and a strong signal. This dye system shows characteristics that make it ideal for ADME and pharmacokinetic studies. Indeed, it was successfully used in CNF ADME studies which showed mDTEB-CNF to be non-toxic.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity). The conjunction "or" is used to link objects of a list or alternatives and is not disjunctive; rather the elements can be used separately or can be combined together under appropriate circumstances.

What is claimed is:

1. A physiologically stable fluorophore for performing fluorescence probing, the physiologically stable fluorophore comprises

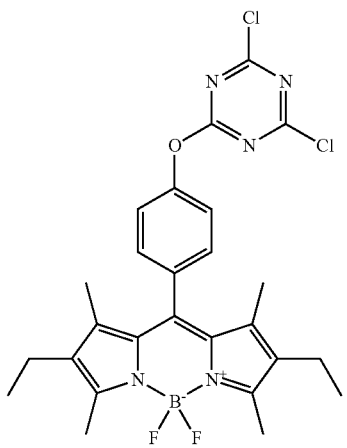

wherein the physiologically stable fluorophore is stable from pH=1 to pH=10 such that the photophysics of the physiologically stable fluorophore is conserved from pH=2 to pH=10.

2. A process for performing fluorescence probing with a physiologically stable fluorophore

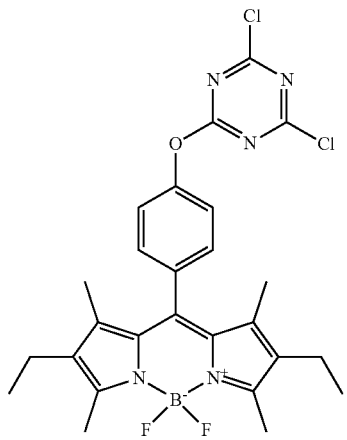

the process comprising: contacting a surface extracted cellulose nanofiber substrate with the physiologically stable fluorophore; forming a fluorophore-substrate complex from the physiologically stable fluorophore and the substrate in response to contacting the substrate with the physiologically stable fluorophore; subjecting the fluorophore-substrate complex to probe radiation; electronically exciting the physiologically stable fluorophore in the fluorophore-substrate complex in response to subjecting the fluorophore-substrate complex to the probe radiation; producing fluorescence from the physiologically stable fluorophore in the fluorophore-substrate complex in response to electronically exciting the physiologically stable fluorophore in the fluorophore-substrate complex; and determining, from the fluorescence from the physiologically stable fluorophore, the redox state of the substrate to perform single-electron transfer fluorescence probing; wherein the physiologically stable fluorophore is stable from pH=1 to pH=10 such that the photophysics of the physiologically stable fluorophore is conserved from pH=2 to pH=10.

* * * * *